US011426379B2

(12) United States Patent
Krueger et al.

(10) Patent No.: US 11,426,379 B2
(45) Date of Patent: Aug. 30, 2022

(54) COMBINATION OF LOCAL AND SYSTEMIC THERAPIES FOR ENHANCED TREATMENT OF DERMATOLOGIC CONDITIONS

(71) Applicants: The Rockefeller University, New York, NY (US); Provectus Pharmatech, Inc., Knoxville, TN (US)

(72) Inventors: James G. Krueger, Rosedale, NY (US); Sandra Garcet, New York, NY (US); Jamie Singer, Knoxville, TN (US); Eric A. Wachter, Oak Ridge, TN (US)

(73) Assignees: Provectus Pharmatech, Inc., Knoxville, TN (US); The Rockefeller University, New York, NY (US)

( * ) Notice: Subject to any disclaimer, the term of this patent is extended or adjusted under 35 U.S.C. 154(b) by 0 days.

(21) Appl. No.: 16/204,832

(22) Filed: Nov. 29, 2018

(65) Prior Publication Data
US 2019/0160039 A1 May 30, 2019

Related U.S. Application Data

(60) Provisional application No. 62/592,086, filed on Nov. 29, 2017.

(51) Int. Cl.
| A61K 31/352 | (2006.01) |
| A61K 9/00 | (2006.01) |
| A61K 45/06 | (2006.01) |
| A61P 17/04 | (2006.01) |
| A61P 17/06 | (2006.01) |
| A61K 31/4035 | (2006.01) |
| A61K 9/06 | (2006.01) |
| A61K 31/52 | (2006.01) |
| A61K 31/69 | (2006.01) |
| A61K 31/519 | (2006.01) |
| A61K 38/13 | (2006.01) |

(52) U.S. Cl.
CPC ......... *A61K 31/352* (2013.01); *A61K 9/0014* (2013.01); *A61K 9/06* (2013.01); *A61K 31/4035* (2013.01); *A61K 31/519* (2013.01); *A61K 31/52* (2013.01); *A61K 31/69* (2013.01); *A61K 38/13* (2013.01); *A61K 45/06* (2013.01); *A61P 17/04* (2018.01); *A61P 17/06* (2018.01)

(58) Field of Classification Search
CPC .... A61K 31/352; A61K 31/4035; A61P 17/06
See application file for complete search history.

(56) References Cited

U.S. PATENT DOCUMENTS

| 2,798,053 A | 7/1957 | Brown et al. |
| 2,909,462 A | 10/1959 | Warfield et al. |
| 3,330,729 A | 7/1967 | Johnson, Jr. |
| 5,556,992 A | 9/1996 | Gaboury et al. |
| 8,974,363 B2 * | 3/2015 | Dees ............ A61K 33/14 600/2 |
| 9,107,887 B2 * | 8/2015 | Eagle ............ C12N 7/00 |
| 2005/0019264 A1 | 1/2005 | Dees et al. |
| 2008/0207738 A1 | 8/2008 | Kiss |

FOREIGN PATENT DOCUMENTS

| JP | 2014-510728 A | 5/2014 |
| WO | 2002/34292 A1 | 5/2002 |
| WO | 2004/044219 A2 | 5/2004 |

OTHER PUBLICATIONS

NCT02322086 (Clinicaltrials.gov, Sep. 15, 2015, 7 pages) (Accessed from https://www.clinicaltrials.gov/ct2/history/NCT02322086?V_5=View#StudyPageTop on Jun. 11, 2020) (Year: 2015).*
Otezla Prescribing Information (Celgene Corporation, Revised Mar. 2014, 9 pages) (Year: 2014).*
Ighani et al. J. Am. Acad. Dermatol., Mar. 2018, vol. 78, No. 3, pp. 623-626 (Published Online Oct. 6, 2017) (Year: 2018).*
International Search Report re application No. PCT/US/2018/063094, dated Mar. 26, 2019.
Written Opinion re application No. PCT/US/2018/063094, dated Mar. 26, 2019.
Pincelli, C. et al, "Mechanisms Underlying the Clinical Effects of Apremilast for Psoriasis," Journal of Drugs in Dermatology, vol. 17, issue 8, Aug. 2018, pp. 835-840.
Patel, S.P. et al, "Percutaneous Hepatic Injection of Rose Bengal Disodium (PV-10) in Metastatic Uveal Melanoma," American Society of Clinical Oncologists, 2020, MUM—May 20, 2020.
Price, T. et al, Abstract No. 1334TiP: "A Phase 1 Study of Oncolytic Immunotherapy of Metastatic Neuroendocrine Tumours Using Intralesional Rose Bengal Disodium," European Society for Medical Oncology (ESMO) Congress 2018, Munich, Germany, Oct. 19-23, 2018.

(Continued)

*Primary Examiner* — James D. Anderson
(74) *Attorney, Agent, or Firm* — Husch Blackwell LLP

(57) ABSTRACT

A treatment for inflammatory dermatoses, such as psoriasis and atopic dermatitis (eczema), is disclosed that utilizes topical administration of a halogenated xanthene, such as rose bengal, together with administration of one or more complementary targeted systemic dermatology therapies, preferably a therapy that addresses the inflammatory pathway and is other than an NSAID that is a COX-1 and/or COX-2 inhibitor. Examples of complementary targeted systemic therapeutic ingredients include: corticosteroids, including betamethasone dipropionate and fluocinonide; dithranol; vitamin D analogs, including calcipotriol; and retinoids, non-biologics including methotrexate, ciclosporin, hydroxycarbamide, and fumarates including dimethyl fumarate; as well as one or more biologics, including antibodies or paratope-containing antibody portions to TNF-α, antibodies to pro-inflammatory cytokines interleukin-12, interleukin-23 and interleukin-17, and TNF inhibitors. Treatment of other epithelial tissue, such as the lining of the gut, is also disclosed.

6 Claims, 21 Drawing Sheets

(56) References Cited

OTHER PUBLICATIONS

Krueger, J.G. et al, Abstract No. 115, poster P013: "Immune Modulation by Topical PH-10 Aqueous Hydrogel (Rose Bengal Disodium) in Psoriasis Lesions," 8th International Psoriasis from Gene to Clinic Congress, London, UK, Nov. 30-Dec. 2, 2017.
Agarwala, S.S. et al, "Patterns of Response for Combination of PV-10 Oncolytic Immunotherapy and Checkpoint Inhibition," poster at Melanoma Bridge 2018—Napoli, Nov. 29-Dec. 1, 2018.
Pilon-Thomas, S. et al, "Efficacy of Intralesional Injection with PV-10 in Combination with Co-Inhibitory Blockade in a Murine Model of Melanoma," poster, Society for the Immunotherapy of Cancer Meeting, National Harbor, MD, Nov. 6-9, 2014.
McClure, S.L. et al, "Comparative Tolerability of Systemic Treatments for Plaque-Type Psoriasis," Drug Safety, vol. 25, No. 13, 2002, pp. 913-927.
Kim, J.E. et al, "Importance of Concomitant Topical Therapy in Moderate-to-Severe Atopic Dermatitis Treated with Cyclosporine," Dermatologic Therapy, vol. 29, 2016, pp. 120-125.
Feldman, S.R. et al, "The Challenge of Managing Psoriasis: Unmet Medical Needs and Stakeholder Perspectives," American Health & Drug Benefits, vol. 9, No. 9, Dec. 2016, pp. 504-513.
Notay, M. et al, "Probiotics, Prebiotics, and Synbiotics for the Treatment and Prevention of Adult Dermatological Diseases," American Journal of Clinical Deramtology, vol. 18, 2017, pp. 721-732.
Lowes, M.A., et al, "Immunology of Psoriasis," Annual Review of Immunology, vol. 32, 2014, pp. 227-255.
Wu, J. et al, "Enhancing the Efficacy of Photodynamic Therapy (PDT) via Water-Soluble pillar[5]arene-based Supramolecule Complexes," The Royal Society of Chemistry, Chem. Commun. vol. 54, 2018, pp. 7629-7632.
Johnson-Huang, L.A. et al, "Effective Narrow-Band Ultraviolet B Radiation Therapy Suppresses the IL-23/IL-17 Axis in Normalized Psoriasis Plaques," Journal of Investigative Dermatology, vol. 130, No. 11, 2010, pp. 2654-2663.
Yao, Y. et al, "Type I Interferon: Potential Therapeutic Target for Psoriasis?" PLoS One, vol. 3, issue 7, Jul. 2008, e2737.
D'Mello, S,A.N. et al, "Signaling Pathways in Melanogenesis," International Journal of Molecular Sciences, vol. 17, 2016, pp. 1144.
Zakostelska, Z. et al, "Intestinal Microbiota Promotes Psoriasis-Like Skin Inflammation by Enhancing Th17 Response," PLoS One, vol. 11, No. 7, Jul. 2016, e0159539.
Kim, J.R. et al, "Synthesis of Antifungal Agents from Xanthene and Thiazine Dyes and Analysis of Their Effects," Nanomaterials, vol. 6, No. 12, 2016, pp. 243.
Wachter, E. et al, "Topical Rose Bengal: Pre-Clinical Evaluation of Pharmacokinetics and Safety," Lasers in Surgery and Medicine, vol. 32, No. 2, 2003, pp. 101-110.
Neckers, D.C., "Rose Bengal," Journal of Photochemistry and Photobiology, A: Chemistry, vol. 47, 1989, pp. 1-29.
Lee, P.C.C. et al, "Laser Flash Photokinetic Studies of Rose Bengal Sensitized Photodynamic Interactions of Nucleotides and DNA," Photchemistry and Photobiology, vol. 45, No. 1, 1987, pp. 79-86.
Diezel, W. et al, "Therapy of Psoriasis by Means of Hematoporphyrin Derivate and Light," Dermatol. Monatsschr., vol. 166, 1980, pp. 793-797.
Neuner, P. et al, "Cytokine Release by Peripheral Blood Mononuclear Cells is Affected by 8-methoxypsoralen Plus UV-A," Photochemistry and Photobiology, vol. 59, No. 2, 1994, pp. 182-188.
Boehncke, W-H. et al, "Treatment of Psoriasis by Topical Photodynamic Therapy with Polychromatic Light," The Lancet, vol. 343, Mar. 26, 1994, p. 801.
Tonogai, Y. et al, "Studies on the Toxicity of Coal-Tar Dyes. I. Photodecomposed Products of Four Xanthene Dyes and their Acute Toxicity to Fish," Journal of Toxicological Sciences, vol. 4, 1979, pp. 115-126.

Heitz, J.R. et al, "Photodegration of Halogenated Xanthene Dyes," Mississippi Agriculture and Forestry Experiment Station (MAFES) publication 8532, 1978, pp. 35-48.
Ranadive, N.S. et al, "Desensitization of Rabbit Skin by Repeated Exposure to UV-Visible Light of Sites Injected with Rose Bengal," Inflammation, vol. 14, No. 2, 1990, pp. 223-237.
Singh, R.J. et al,"Interaction of Nitric Oxide with Photoexcited Rose Bengal: Evidence for One-Electron Reduction of Nitric Oxide to Nitroxyl Anion," Archives of Biochemistry and Biophysics, vol. 324, No. 2, Dec. 20, 1995, pp. 367-373.
Zamani, S. et al, "Rose Bengal Suppresses Gastric Cancer Cell Proliferation via Apoptosis and Inhibits Nitric Oxide Formation in Macrophages," Journal of Immunotoxicology, 2014 (early online: 1-9), DOI:10.3109/1547691X,2013.853715.
Kim, J. et al, "The Spectrum of Mild to Severe Psoriasis Vulgaris is Defined by a Common Activation of IL-17 Pathway Genes, but with Key Differences in Immune Regulatory Genes," Journal of Investigative Dermatology, vol. 136, 2016, pp. 2173-2182.
Krueger, J.G. et al, "Anti-IL-23A mAb BI 655066 for Treatment of Moderate-to-Severe Psoriasis: Safety, Efficacy, Pharmacokentics, and Biomarker Results of a Single-Rising-Dose, Randomized, Double-Blind, Placebo-Controlled Trial," Journal of Allergy and Clinical Immunology, vol. 136, No. 1, 2015, pp. 116-124.
Nunoya, T. et al, "Use of Miniature Pig for Biomedical Research, with Reference to Toxicologic Studies," Journal of Toxicolgic Pathology, vol. 20, 2007, pp. 125-132.
Berge, S.M. et al, "Pharmaceutical Salts," Journal of Pharmaceutical Sciences, vol. 66, No. 1, Jan. 1977, pp. 1-19.
Fuentes-Duculan, J. et al, "A Subpopulation of CD163 Positive Macrophages is Classically Activated in Psoriasis," Journal of Investigative Dermatology, vol. 130, No. 10, 2010, pp. 2412-2422.
Guttman-Yassky, E. et al, "Low Expression of the IL-23/Th17 Pathway in Atopic Dermatitis Compared to Psoriasis," Journal of Immunology, vol. 181, 2008, pp. 7420-7427.
Suarez-Farinas, M. et al, "Harshlight: A "Corrective Makeup" Program for Microarray Chips," BMC Bioinformatics, vol. 6, Dec. 10, 2005, p. 294.
Kivelevitch, D.N. et al, "Emerging Topical Treatments for Psoriasis," Expert Opinion on Emerging Drugs, Informa UK Ltd., vol. 18, No. 4, pp. 523-532, 2013.
Tan, K-W. et al, "Novel Systematic Therapies for the Treatment of Psoriasis," Expert Opinion on Pharmacotherapy, UK, vol. 17, No. 1, pp. 79-92, 2016.
Supplementary European Search Report re application No. EP 18882370.2, dated Jun. 25, 2021.
Benson, J.M. et al, "Therapeutic Targeting of the IL-12/23 Pathways: Generation and Characterization of Ustekinumab," Nature Biotechnology, vol. 29, No. 7, pp. 615-624, Jul. 2011 (doi: 10.1038/nbt.1903).
Stavre, Z. et al, "Differential Effects of Inflammation on Bone and Response to Biologies in Rheumatoid Arthritis and Spondyloarthritis," Current Rheumatology Reports, vol. 18, No. 72, pp. 1-13, 2016 (doi: 10.1007/s11926-016-0620-x).
Japanese Office Action re application No. JP 2020-529170, dated Aug. 31, 2021 (with English translation).
Celgene Corporation "OTEZLA" label, Sep. 2014.
Borisy, A.A. et al, "Systematic Discovery of Multicomponent Therapeutics," PNAS, vol. 100, No. 3, pp. 7977-7982, Jun. 24, 2003 (www.pnas.org/cgi/doi/10.1073/pnas.1337088100).
Cokol, M. et al, "Systematic Exploration of Synergistic Drug Pairs," Molecular Systems Biology, vol. 7, No. 544, pp. 1-9, 2011; doi:10.1038/msb.2011.71.
Novartis Pharmaceuticals, "PASI Scores, Measuring Skin Clearance for Psoriasis Patients in Clinical Trials," pp. 1-2, Jan. 2015.
Yin, N. et al, "Synergistic and Antagonistic Drug Combinations Depend on Network Topology," PLoS One, vol. 9, issue 4, pp. 1-7, Apr. 2014; doi:10.1371/journal.pone.0093960.
CV, James G. Krueger, MD, PhD., 54 pages, Sep. 2021.
Zhang, P. et al, "A Clinical Review of Phototherapy for Psoriasis," Lasers Med Sci, vol. 33, pp. 173-180 (2018).
Kim, J. et al, "The Spectrum of Mild to Severe Psoriasis Vulgaris is Defined by a Common Activation of IL-17 Pathway Genes, but

(56) References Cited

OTHER PUBLICATIONS with Key Differences in Immune Regulatory Genes," Journal of Investigative Dermatology, vol. 136, pp. 2173-2182 (2016).

Wachter, E. et al, "Topical Rose Bengal: Pre-Clinical Evaluation of Pharmacokinetics and Safety," Lasers in Surgery and Medicine, vol. 32, No. 2, pp. 101-110 (2003).

Liu, H. et al, "Intralesional Rose Bengal in Melanoma Elicits Tumor Immunity via HMGB1," Journal for ImmunoTherapy of Cancer, vol. 3, suppl. 2, p. 408 (2015).

Toomey, P. et al, "Intralesional Injection of Rose Bengal Induces a Systemic Tumor-Specific Immune Response in Murine Models of Melanoma and Breast Cancer," PLOS One, vol. 8, issue 7, e68561 (2013).

Thompson, J.F. et al, "Phase 2 Study of Intralesional PV-10 in Refractory Metastatic Melanoma," Annals of Surgical Oncology, vol. 22, pp. 2135-2142 (2015). DOI 10.1245/s10434-014-4169-5.

Liu, H. et al,, "Intralesional Rose Bengal in Melanoma Elicits Tumor Immunity via Activation of Dendritic Cells by the Release of High Mobility Group Box 1," Oncotarget, vol. 7, No. 25, pp. 37893-37905, (2016). doi:10.18632/oncotarget.9247.

Remicade® (infliximab) Package Insert at Paragraph 14.8; (Nov. 2013).

Humira® (adallimumab) Package insert Paragraph 14.6; (Mar. 2011).

Puig, L. et al, "Update on Topical Treatments for Psoriasis: The Role of Calcipotriol Plus Betamethasone Dipropionate Aerosol Foam," Actas Dermosifiliogr., vol. 110, No. 2, pp. 115-123 (2019). https://doi.org/10.1016/j.adengl.2019.01.001.

Dorland's Illustrated Medical Dictionary, 29th ed. W.B Saunders Company, Philadelphia, p. 926, (2000).

Czarnecka-Operacz, M. et al, "The Possibilities and Principles of Methotrexate Treatment of Psoriasis—The Updated Knowledge," Postep Derm Alergol, vol. 6, pp. 392-400 (Dec. 6, 2014). DOI: 10.5114/pdia.2014.47121.

Cyclosporine Package insert at "Description" (Sep. 2009).

Sulfasalazine Package insert at "Description" (2009).

Zaba, L.C. et al, "Amelioration of Epidermal Hyperplasia by TNF Inhibition is Associated with Reduced Th17 Responses," Journal of Experimental Medicine, vol. 204, No. 13, pp. 3183-3194 (Dec. 24, 2007). www.jem.org/cgi/doi/10.1084/jem.20071094.

Gudjonsson, J.E. et al, "Novel Systemic Drugs Under Investigation for the Treatment of Psoriasis," J Am Acad Dermatol, vol. 67, No. 1, pp. 139-147 (Jul. 2012). doi:10.1016/j.jaad.2011.06.037.

Schafer, P.H. et al, "Novel Systemic Drugs for Psoriasis: Mechanism of Action for Apremilast, a Specific Inhibitor of PDE4," J Am Acad Dermatol, vol. 68, No. 6, pp. 1041-1042 (Jun. 2013).

Perez-Aso, M. et al, "Apremilast, a Novel Phosphodiesterase 4 (PDE4) Inhibitor, Regulates Inflammation Through Multiple cAMP Downstream Effectors," Arthritis Research & Therapy, 17:249 (2015). DOI 10.1186/s13075-015-0771-6.

\* cited by examiner

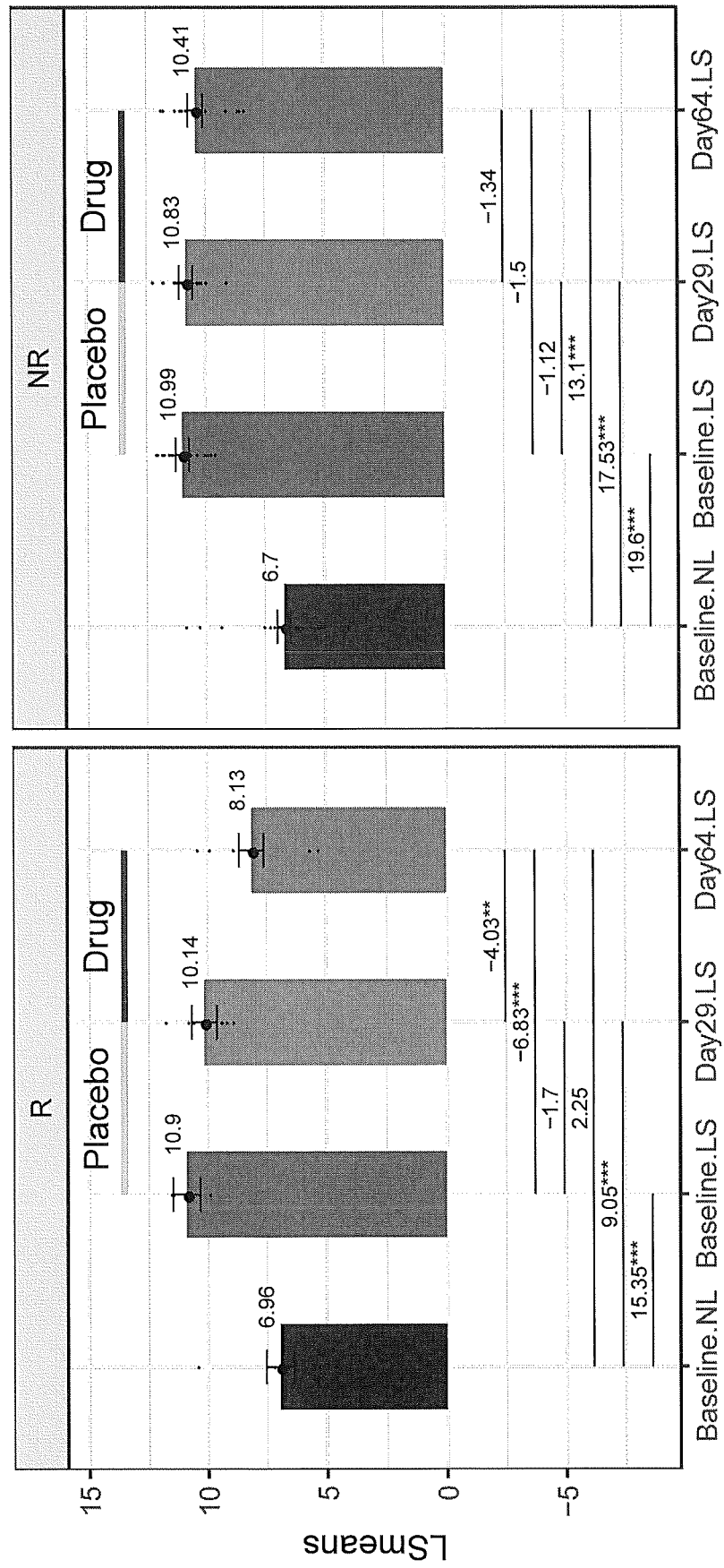

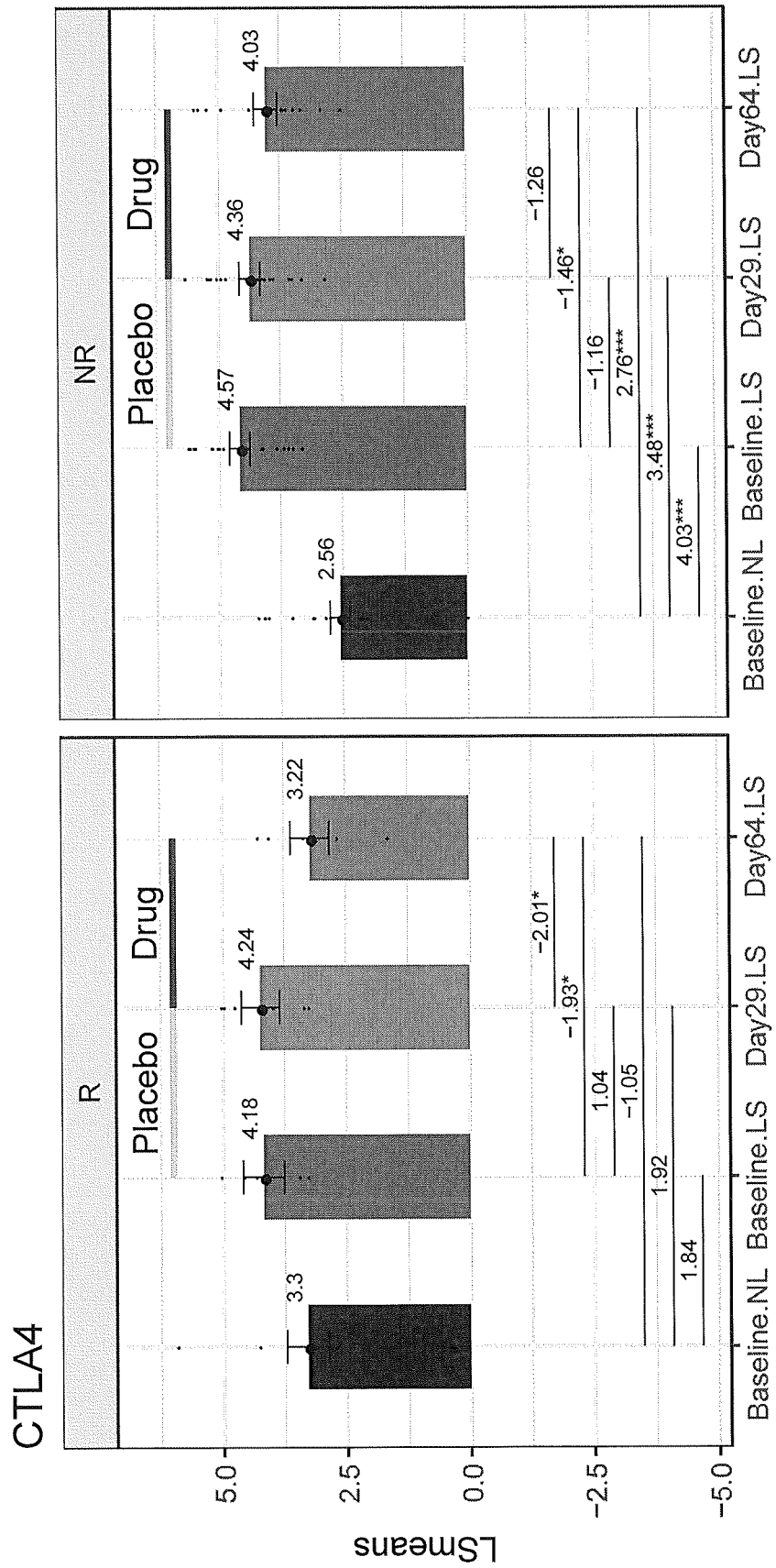

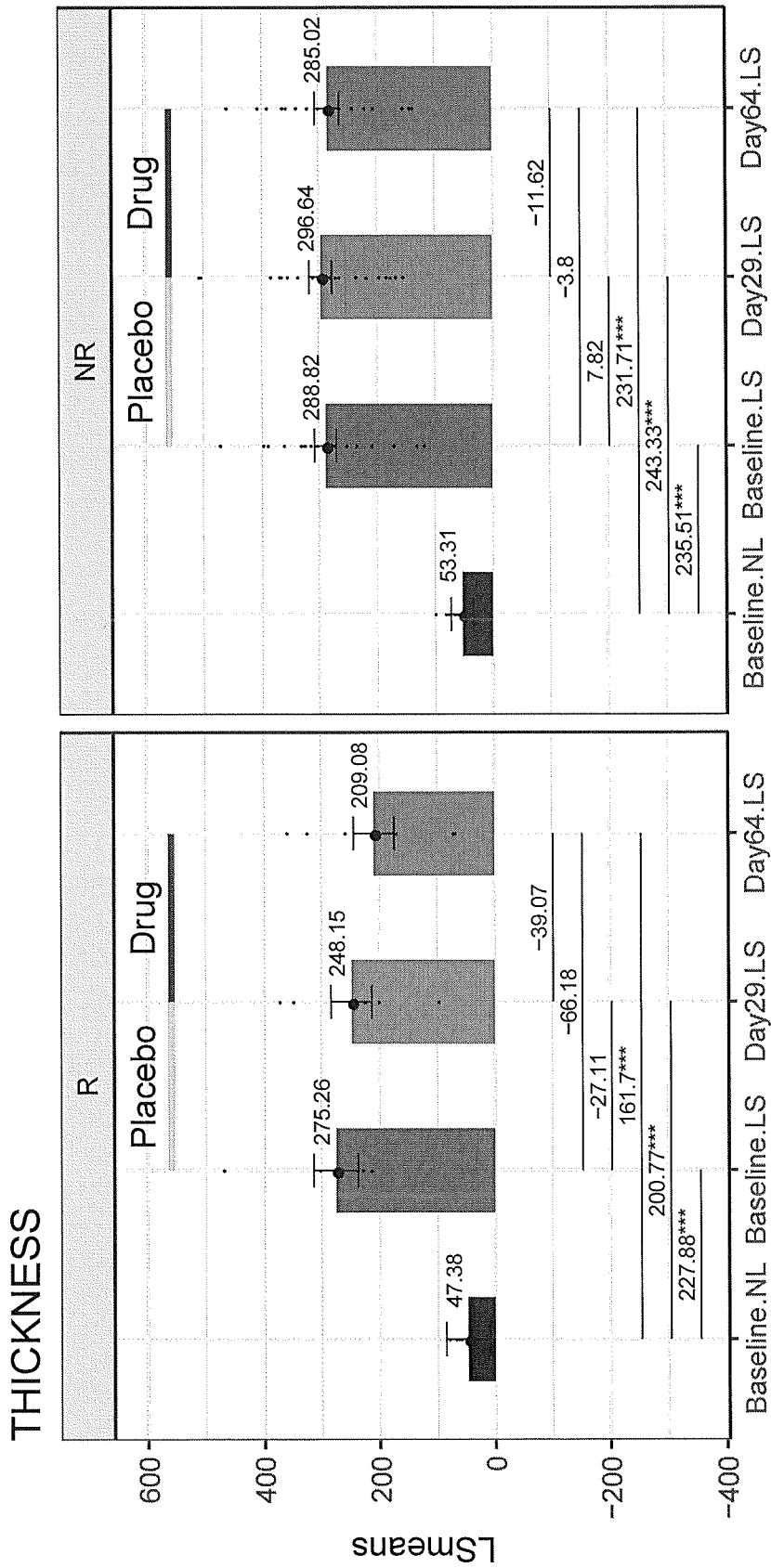

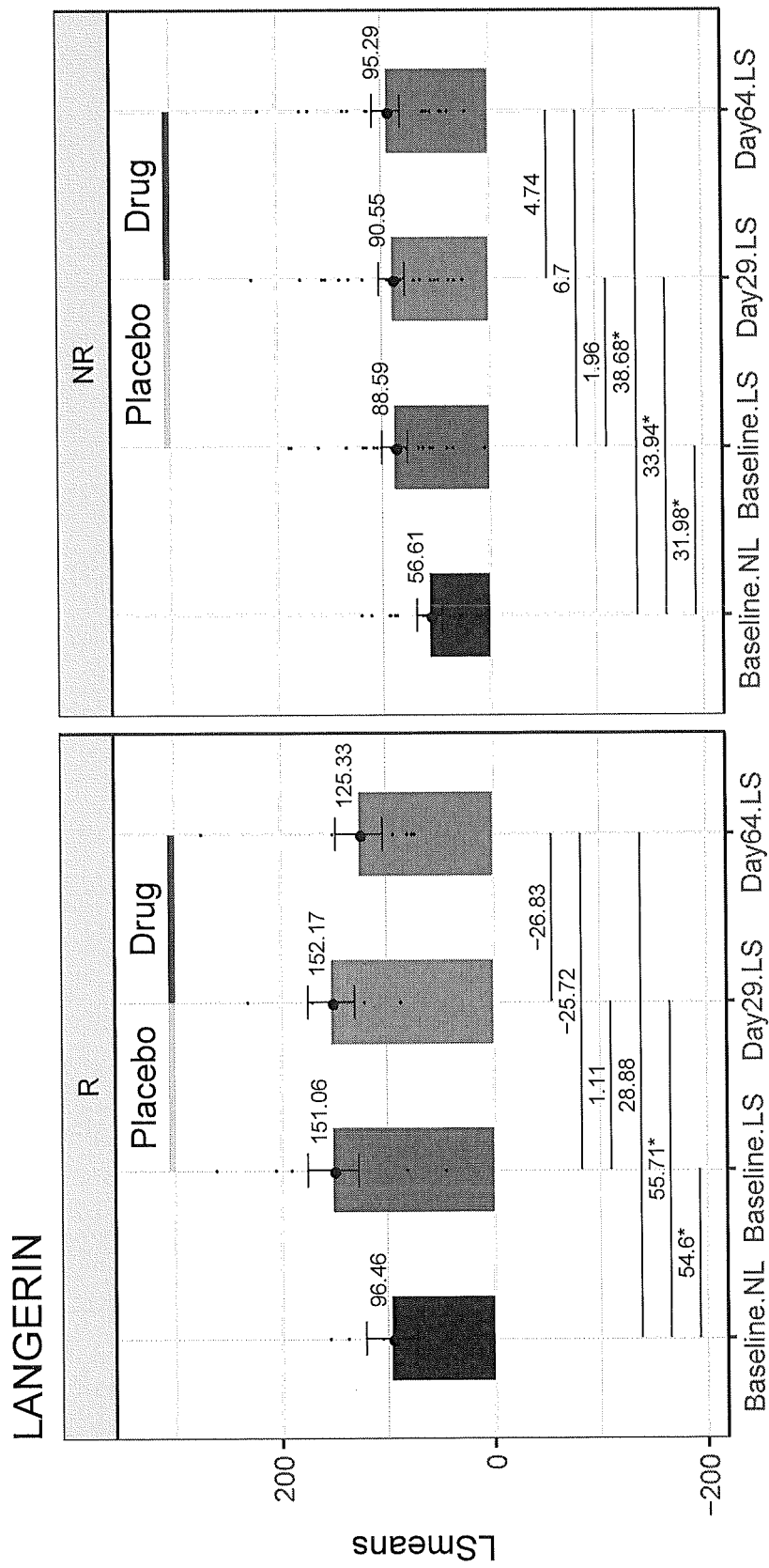

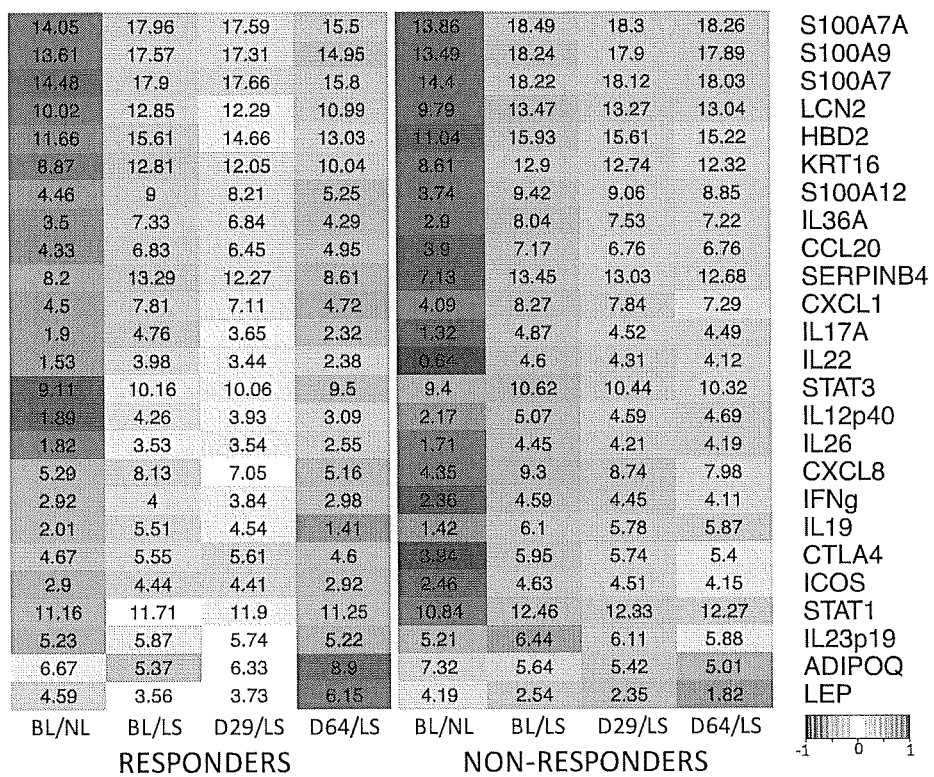

COMBINATION OF LOCAL AND SYSTEMIC THERAPIES FOR ENHANCED TREATMENT OF DERMATOLOGIC CONDITIONS

CROSS-REFERENCE TO RELATED APPLICATION

This application claims priority to U.S. provisional application Ser. No. 62/592,086, filed on Nov. 29, 2017, whose disclosures are incorporated herein by reference.

FIELD OF THE INVENTION

This invention relates to the fields of dermatology and improved therapeutic regimens therefore.

BACKGROUND OF THE INVENTION

Pharmacologic approaches for treating hyperproliferative or inflammatory dermatologic conditions have traditionally relied on the use of various single agent systemic therapies, single agent topical therapies (monotherapies), or other locally administered modalities like light therapy, all in a rotation to avoid toxicity or intermittently to reduce inflammation and address symptoms which appear often sporadically. These diseases are chronic, lifelong and are difficult to manage.

The underlying disease triggers are difficult to predict and address and lead to a challenge for interventions prior to manifestation of widespread symptoms. In the management of these diseases, it is often necessary to monitor patients for side effects of the drugs, as is the case with cyclosporine and methotrexate in psoriasis (McClure et al., 2001 Drug Safety 25:913-927) or rotate drugs in sequential or intermittent approaches to avoid toxicity or increase compliance.

Both in psoriasis and atopic dermatitis, T-cells drive the disease in patients. Typical treatments are targeted to the underlying inflammation or proliferation of skin cells or reducing overactive immune cell function. Topical steroids are the most common prescribed treatment for hyperproliferative skin disorders; however, extended use of topical corticosteroid creams may cause thinning of the skin, stretch marks and have systemic effects. Topical calcineurin inhibitors have been implicated in rare cases of malignancy.

So-called PUVA treatment involves the use of psoralen and exposure to UVA light (long wavelength ultraviolet light) administered to the skin. This treatment has the drawback of increasing aging of the skin and susceptibility to skin cancer as well as inconvenience for the patient to attend multiple light therapy sessions in the physician's office.

Topical and oral phosphodiesterase-4 inhibitors have also been used to target immune cells in these conditions. Methotrexate, cyclosporine, fumaric acid esters, acitretin, alefacept are small molecule approaches to addressing these diseases, all with different levels of side effects and efficacy.

Newer biologic agents like adalimumab, guselkumab, efalizumab, etanercept, infliximab, abatacept, golimumab and ustekinumab are expensive and have different sets of side effects, notably latent tuberculosis reactivation, increase risk of infection, exacerbation of demyelinating conditions, liver toxicity and cardiovascular complications.

Subsets of patients do not improve after single agent therapy directed toward inflammatory pathways like TNF-alpha inhibition (e.g. guselkumab, infliximab, adalimumab, certolizumab pegol, and golimumab), IL-17A inhibition (secukinumab and ixekizumab), IL-6 inhibition (sarilumab) and IL-12/IL-23 inhibition and inhibition of the alpha-subunit of IL-23, p19, with the newest biologic agents (guselkumab). This type of "mixed" response outcome occurs with other topical or systemic drugs now approved for psoriasis, eczema or actinic keratoses, highlighting a need to personalize treatments and potentially to have predictive response biomarkers for individual drugs.

Of the above cited active agents, efalizumab and alefacept, have been discontinued.

More skin conditions may not be completely responsive to such monotherapy, either due to systemic toxicity necessitating lower dosages or development of resistance that circumvents the activity of the monotherapy agent. Additionally, there are ethnic differences in manifestations and genetic drivers of hyperproliferative skin disorders and for example, age differences in the pathogenesis of atopic dermatitis (AD) depending on manifestations in childhood or adulthood. This is further complicated by the lack of clinical studies in children's AD as they are often prescribed medicines approved initially in adults whose underlying disease is potentially driven by other inflammatory markers. Because of these issues there is considerable room for improvement in terms of efficacy and safety.

Use of a combination of topical agents in eczema has shown some promise (Kim et al., *Dermatol Ther.* 2016 March-April; 29(2):120-125), and combinations are often used in psoriasis (Feldman et al., *Am Health Drug Benefits* 2016 Dec. 9(9):504-513); however, many of these combinations do not achieve a satisfactory response.

Oral probiotics, prebiotics and synbiotics have even been used in both psoriasis and eczema and resulted in some skin symptom improvements (Notay et al., *Am J Clin Dermatol.* 2017 18(6):721-732).

Therapeutic strategies to locally address immune cell dysfunction in the skin underlying psoriasis without systemic immune suppression are highly sought after in development of therapeutics (Lowes et al., *Annu Rev Immunol* 2014 32: 227-255). One method, currently in use, is photodynamic therapy (PDT), including UVB first line therapy (Wu et al., *Chem Commun* 2018 54:7629-7632). These therapies have been shown to normalize psoriasis histology by inducing apoptosis of T-cells and keratinocytes resulting in a reduction of myeloid inflammatory dendritic cells, and pathologic cytokines (IL-17, INF-gamma and IL-22) [Johnson-Huang et al., *J Invest Derm* 2010 130(11):2654-2663].

To better understand potential immune-drug targets in psoriasis, investigators have compared lesional and non-lesional skin for immune markers and genetic overexpression in psoriasis lesions, implicating mDCs, CD4$^+$ T-cells and overexpression of INF-gamma inducible genes in lesional skin [Yao et al., *PLos One* Jul. 16, 2008, 3(7): e2737]. In this study, lesional and non-lesional skin biopsies were compared to elucidate cellular and biochemical markers of disease.

Further complicating the therapeutic challenge dermatologic conditions, potentially in response to stimuli in the gut. Studies have shown that gut bacteria play a role in the development of eczema (D'Mello et al., *Int J Mol Sci.* 2016 July; 17(7):1144) where it may play a role in psoriasis by promoting a TH17 response (Zákostelská et al., *PLoS One.* 2016 Jul. 19; 11(7):e0159539).

Regardless of the cause, once an aberrant immune-inflammatory response starts, it is difficult to stop with conventional therapies.

The use of disease cell-specific xanthenes delivered topically is a novel hybrid approach that has been described by one or more of the present inventors (for example in U.S.

Pat. No. 8,974,363), whose disclosures are incorporated herein in their entirety). This approach maximizes topical efficacy, while minimizing systemic exposure of the patient to the applied agent and resultant potential for systemic adverse effects.

One or more of the present inventors have shown that topical use of a certain specific class of agent (for example certain formulations of certain halogenated xanthenes, exemplified by a 0.001% to 10% solution of rose bengal disodium in saline, termed "PH-10" and undergoing clinical testing for treatment of psoriasis and eczema) can elicit not only abatement of hallmark symptoms like pruritus and erythema in these conditions, but also direct modification on the underlying genes causative of the condition that can lead to long term abatement of the disorder. It is likely that targeting of the improper signaling of keratinocytes with topical PH-10 informs an immune response that can affect local inflammation, and may serve an adjuvant role in promoting specific disease response. Additionally, halogenated xanthenes have antimicrobial (e.g., antibacterial, antifungal and/or anti-parasitic) properties (Kim et al., *Nanomaterials* (Basel). 2016 December; 6(12):243) that could impact the underlying driver of disease.

PH-10 is a topical hydrogel formulation that yields selective delivery of rose bengal disodium to epithelial tissues [Wachter et al., *Lasers Surg Med* 2003 32(2):101-110]. In vitro studies demonstrate that rose bengal can be photoactivated at either very low concentrations or when exposed to relevant wavelengths of light when present in biological systems. Photoactivation of rose bengal produces singlet oxygen (Neckers, *J Photochem Photobiol A* 1989 47:1-29; Lee et al., *Photochem Photobiol* 1987 45(1):79-86) and may induce selective local cellular disruption in target tissue, leading to cell death and/or release of cytokine mediators involved in a beneficial immune response following photodynamic therapy (Diezel et. al., *Dermatol Monatsschr* 1980; 166:793-797; Neuner et al., Photochem Photobiol 1994; 59:182-188; Boehncke et al., *Lancet* Mar. 26, 1994 343: 801).

Upon continued illumination in biological systems, rose bengal may photobleach to an inactive state (Tongai et al., *J Toxicol Sci* 1979; 4:115-125; Heitz and Wilson, *Mississippi Agriculture and Forestry Experiment Station Publication* 1978; 8532:35-48) potentially yielding self-limited photoactivation activity. Additionally, intradermal injection of rose bengal in the presence of light led to polymorphonuclear leukocyte accumulation and histamine release with accompanying increased erythema in rabbit skin. This effect was reversible with co-administration of beta-carotene (Ranadive et al., *J Nutr* 1989 119:690-701).

Additionally rose bengal-generated free radicals have been implicated in nitric oxide consumption with light irradiation (Singh et al., *Arch Biochem Biophys* 1995 324 (2):367-373) and without light irradiation in macrophages (Zamani et al., *J Immunotoxicol* 2014 11(4):367-375). Recent clinical studies have been evaluating rose bengal in dermatologic conditions such as psoriasis (NCT01247818, NCT00941278) and atopic dermatitis (NCT00690807) without active light activation.

SUMMARY OF THE INVENTION

The present invention is the result of unanticipated and unpredicted synergy resulting upon combination of certain local therapeutic modalities, and in particular certain local immunomodulative therapies such as antimicrobial- or keratinocyte-directed treatment using a halogenated xanthene agent such as that referred to under the name PH-10, with an effective amount of one or more certain systemic therapeutic modalities. This combination can boost the therapeutic activity of both therapeutic modalities with the potential for no significant increase, or even an overall decrease, in morbidity relative to that typically achieved using the component therapies separately.

Halogenated xanthenes, delivered topically, can lead to rapid abatement of pruritus in both atopic dermatitis and psoriasis, as well as clearance of skin disease after 28 days of treatment. This rapid abatement of pruritus is beneficial to the patient and is accompanied by limited systemic exposure to the halogenated xanthene, as halogenated xanthenes do not transit the skin and surrounding or systemic tissue that is not exposed. This limited systemic halogenated xanthene exposure could be due to the antimicrobial activity (i.e., antibacterial, antifungal and/or anti-parasitic activity) of the halogenated xanthenes or to known immunomodulatory activity of halogenated xanthenes (U.S. Pat. No. 9,107,887). Regardless of the cause, certain genetic markers change after such treatment, and the resultant genetic markers that change indicate that these halogenated xanthenes surprisingly do not act through usual anti-inflammatory genes or in the same manner as current therapies, but act rather on alternative genes that are causative of or contribute to the inflammatory skin dermatoses.

However, for usual usage, as well as for cases where disease is widely disseminated, severe, or presents in a form difficult to fully cover with a topical agent, use of a complementary therapeutic modality offers synergistic benefit, particularly when it contributes anti-inflammatory activity that complements the activity afforded through topical application of halogenated xanthenes. The use of such complementary therapies can have further advantage in terms of synergistic interactions that permit one or both therapies to be used at reduced doses or shorter in duration (relative to that needed when used individually as monotherapies), while retaining high efficacy, thereby reducing undesirable adverse effects.

In particular, the use of a potent topical therapy directed toward the autoimmune response-causing hyperproliferation of skin cells, such as topical application with, for example, PH-10 or another halogenated xanthene-containing composition, in conjunction with one or more systemic dermatology therapies (especially those that address one or more inflammatory pathway) is highly attractive because this combination yields a uniquely salubrious combination: exposure of the patient's skin disease to a halogenated xanthene's antimicrobial effects in addition to keratinocyte modulatory effects in the presence of systemic anti-inflammatory or biologic targeted to an anti-inflammatory pathway. The effects of such combination can be heightened before, at the time of administration of the halogenated xanthene or subsequent to topical administration.

Because topical application is suited to repeat treatment, continued potentiation of the underlying inflammation, for example by continued administration of the systemic immunomodulatory therapy, while a topical xanthene is administered one or more times, is a preferred embodiment. As an alternate embodiment, topical administration of a xanthene can be followed by commencement of systemic anti-inflammatory therapy.

The benefits of combining local skin therapy with a systemic anti-inflammatory therapy regimen can make otherwise undesirable systemic therapies viable. Thus, because of the resultant augmentation in potency of the systemic component of the combination therapy, reduced systemic dose regimens can be possible with commensurate reduction in adverse effects from the systemic therapy. Further, because the adverse effect profile of the local therapy (i.e., topical xanthene) is non-overlapping to that of most systemic therapies, a combined local and systemic dermatologic therapy is inherently safer and more attractive compared with prior combinations that can produce undesirable synergistic adverse effects.

In addition to applicability to skin, the present invention is applicable to disease of other epithelial tissue, such as that of the lining of the gut or reproductive tract.

BRIEF DESCRIPTION OF THE DRAWINGS

In the drawings forming a portion of this description,

FIGS. 2A and 2B through FIGS. 7A and 7B show the identities of mRNA gene markers of individual genes related to psoriasis as noted near the top of each figure (KRT16, CTLA4, IL19, S100A12, S100A7A, and IL36A, respectively) whose expressed mRNA amounts were normalized at day 64 in responders (R; 2A) and non-Responders (NR; 2B), etc.; least squares mean mRNA log 2 (expression/hARP) levels (qRT-PCR) by molecular response cohort (Responders and Non Responders) in non-lesional (NL) and lesional (LS) psoriasis skin at different time points (baseline, day 29 and day 64). Asterisks indicate statistically significant differences between the groups * $p<0.05$,  $p<0.01$, * $p<0.001$;

FIGS. 8A and 8B through FIGS. 11A and 11B show decreased expression of immunohistochemistry markers (Thickness, Langerin, CD3, CD11, respectively) as identified near the top of each figure in Responder (R; A) and Non-Responder (NR; B) in non-lesional (NL) and lesional (LS) psoriasis skin at different time points (baseline, day 29 and day 64) in patients treated with PH-10. Asterisks describe statistically significant differences between the groups * $p<0.05$,  $p<0.01$, * $p<0.001$);

FIGS. 19A and 19B are Heatmap summaries of least squares mean mRNA log 2 (expression/hARP) levels (qRT-PCR) by molecular response cohort in non-lesional (NL) skin and lesional (LS) psoriasis skin at baseline (BL), day 29 (D29) and day 64 (D64) for Responders 19A) and Non-Responders (19B), analyzed similarly to the data presented in Kim et al., *J Invest Dermatol* 2016 136:2173-2182 and Krueger et al., *J Allergy Clin Immunol* 2015 136(1):116-124;

DETAILED DESCRIPTION OF PREFERRED EMBODIMENTS

Figure 1:
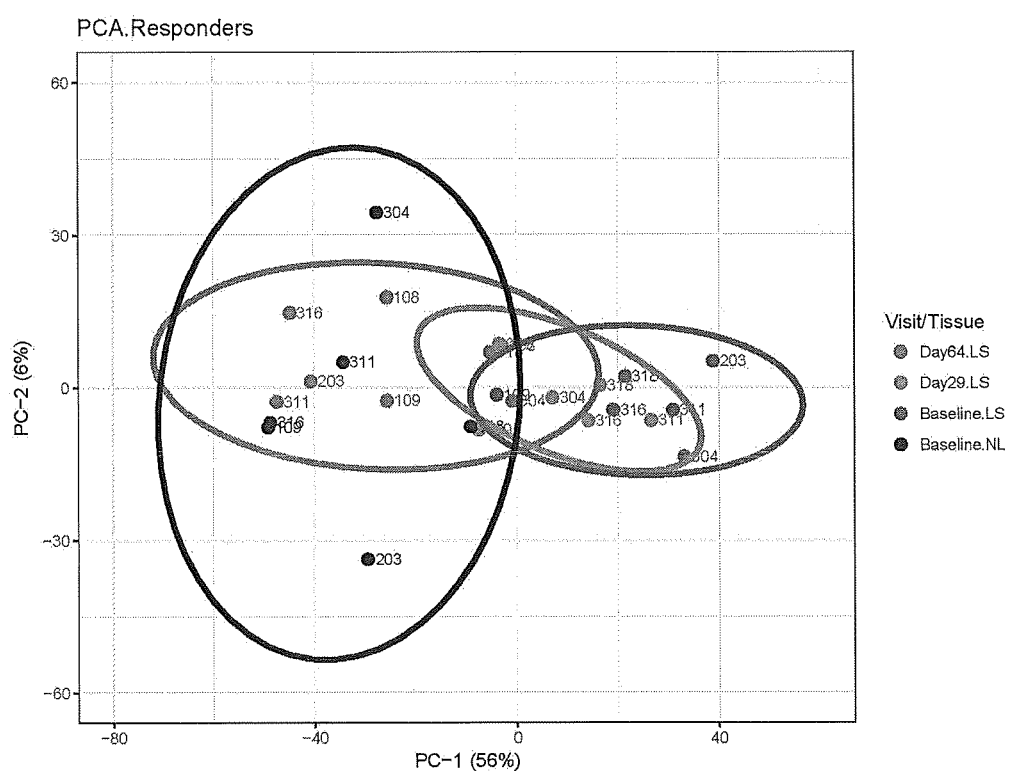
FIG. 1 illustrates the biopsy analysis by principal component analysis (PCA) of gene array results of a subset of human psoriasis patients whose lesional skin (LS) responded (responders) to topical xanthene treatment with PH-10. Gene expression markers of hyperproliferative skin disorders were compared using 1) non-lesional skin on day 1 baseline (Baseline.NL); 2) lesional psoriasis skin at day 1 (Baseline.LS), after 28 days of application of the formulation vehicle (Day29.LS), and after topical xanthene treatment with the 0.005% rose bengal for 28 days that followed six days of no treatment (Day64.LS). Day 64 lesional skin is clustering with characteristics of baseline non-lesional skin. Three digit numbers are patient identifiers. Assays were equivalent to those discussed in Kim et al., *J Invest Dermatol* 2016 136:2173-2182 and Krueger et al., *J Allergy Clin Immunol* 2015 136(1):116-124.
Figure 4A:
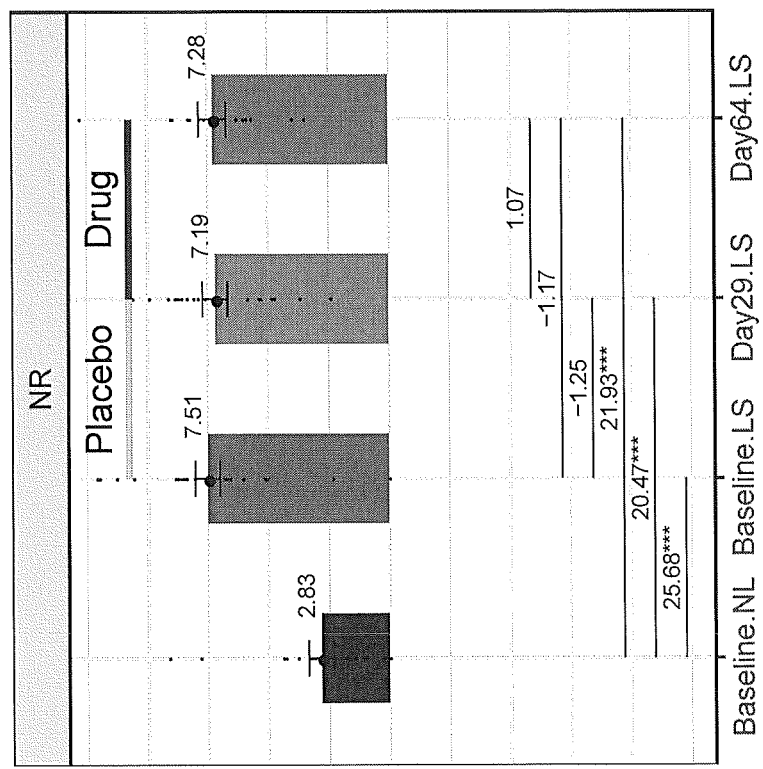
Figure 4B:
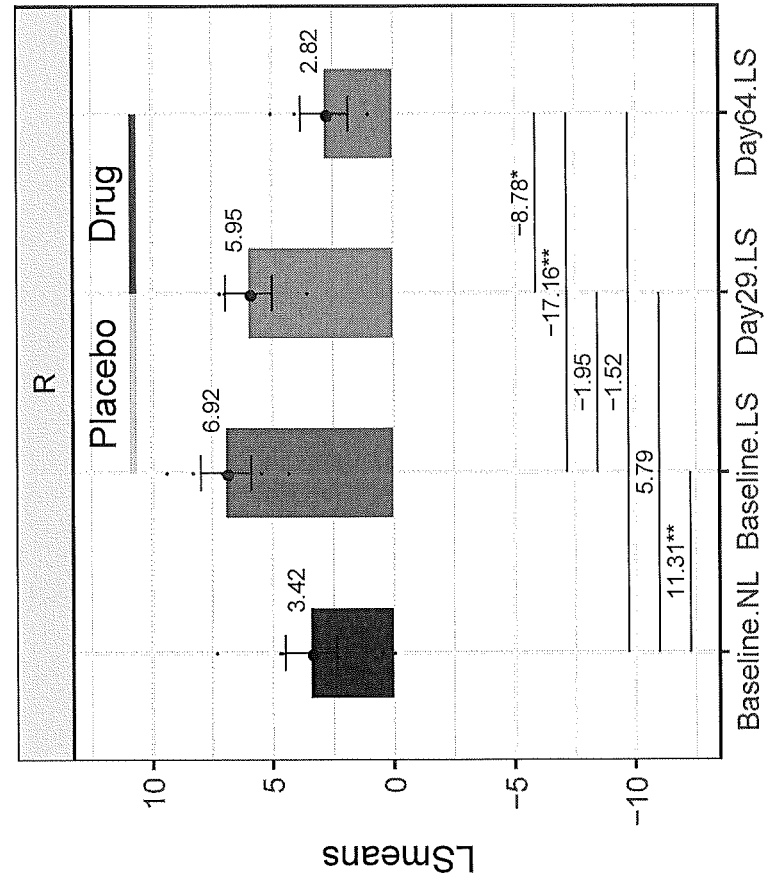
Figure 5A:
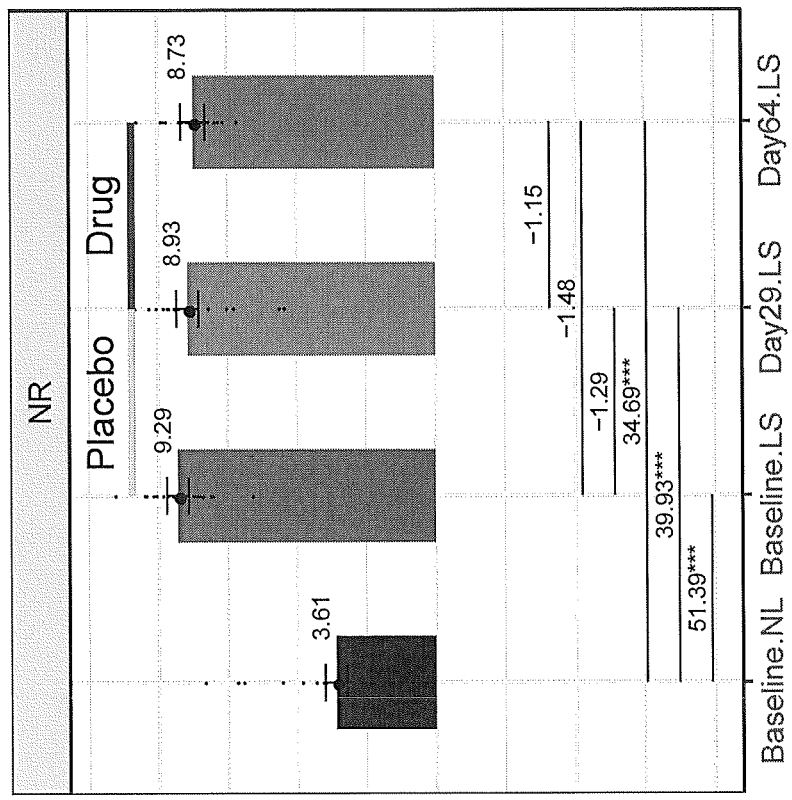
Figure 5B:
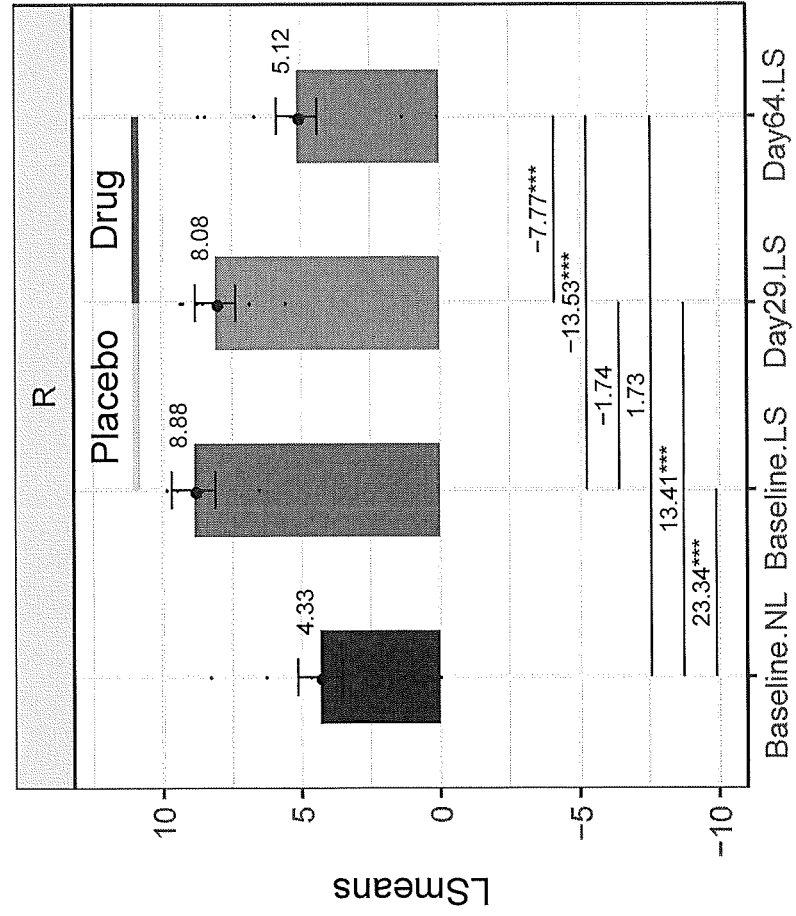
Figures 6A, 6B:
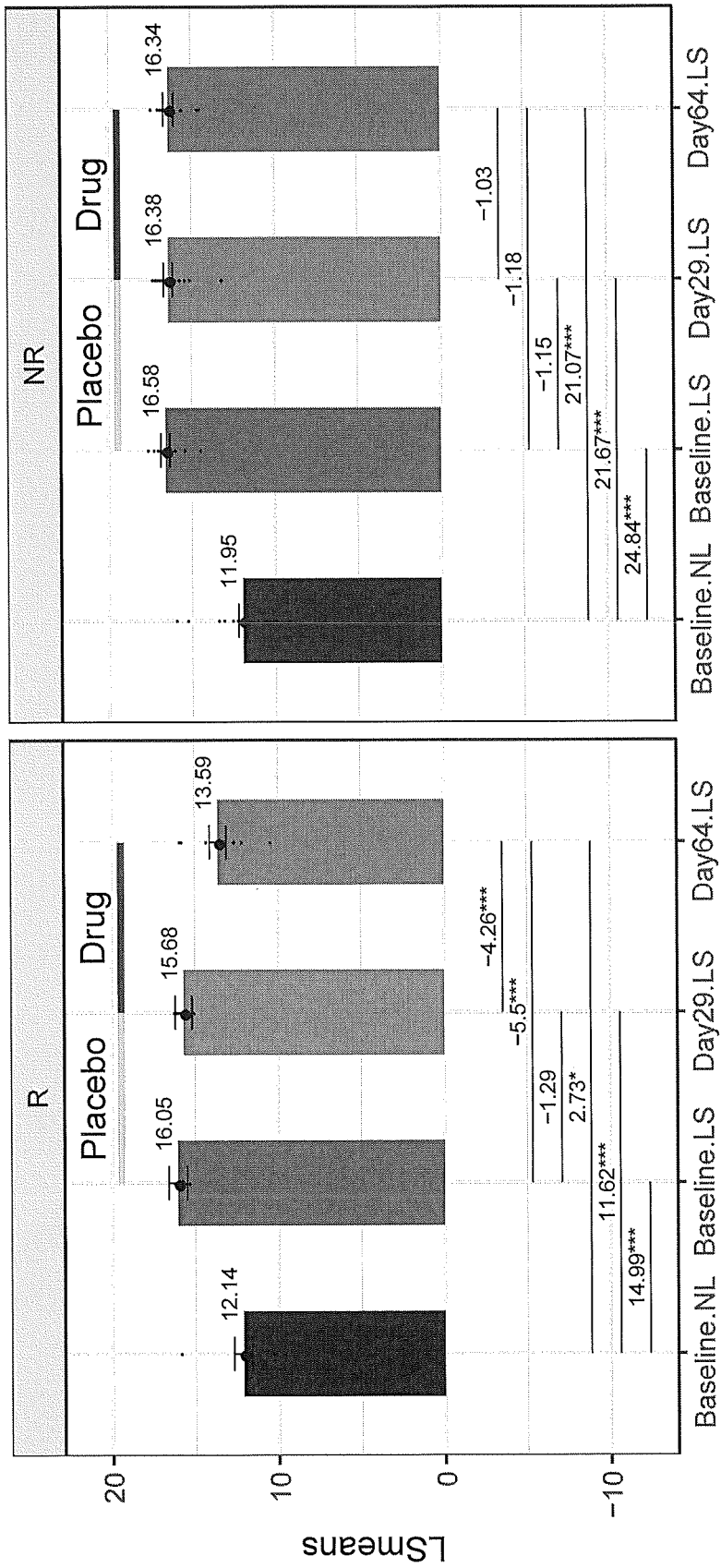
Figure 7A:
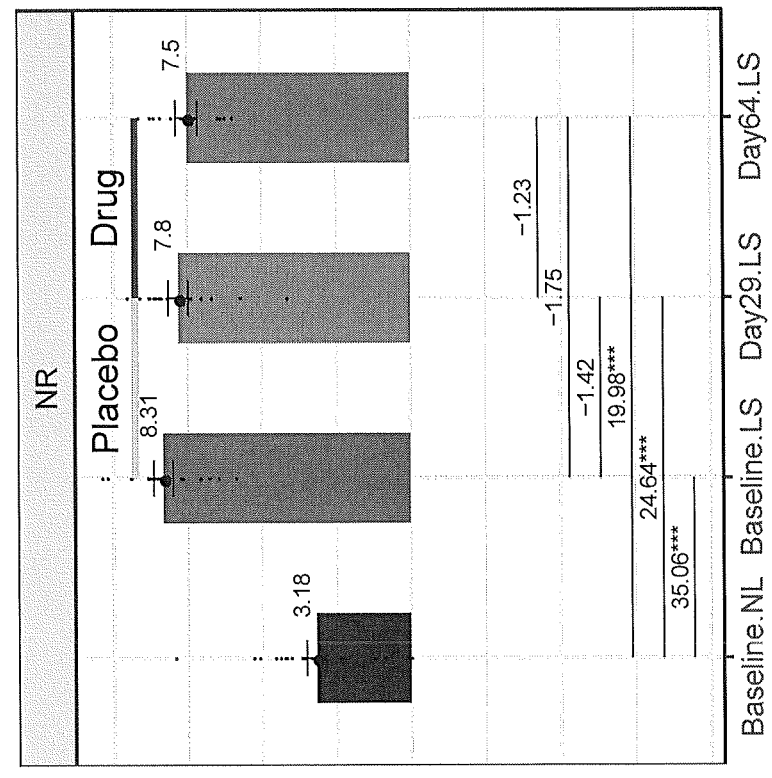
Figure 7B:
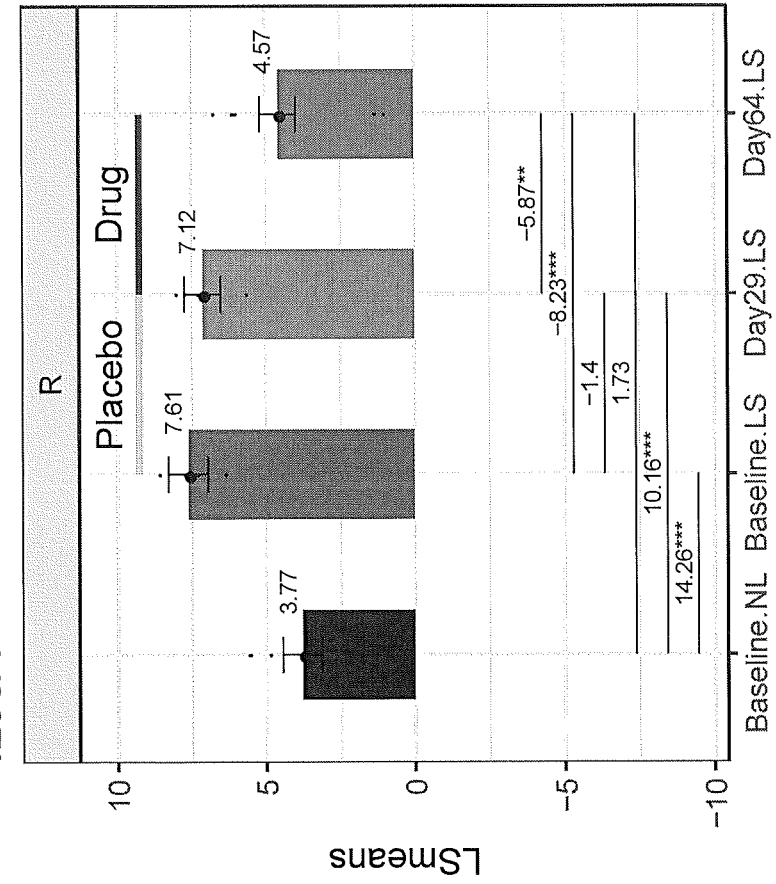
Figures 10A, 10B:
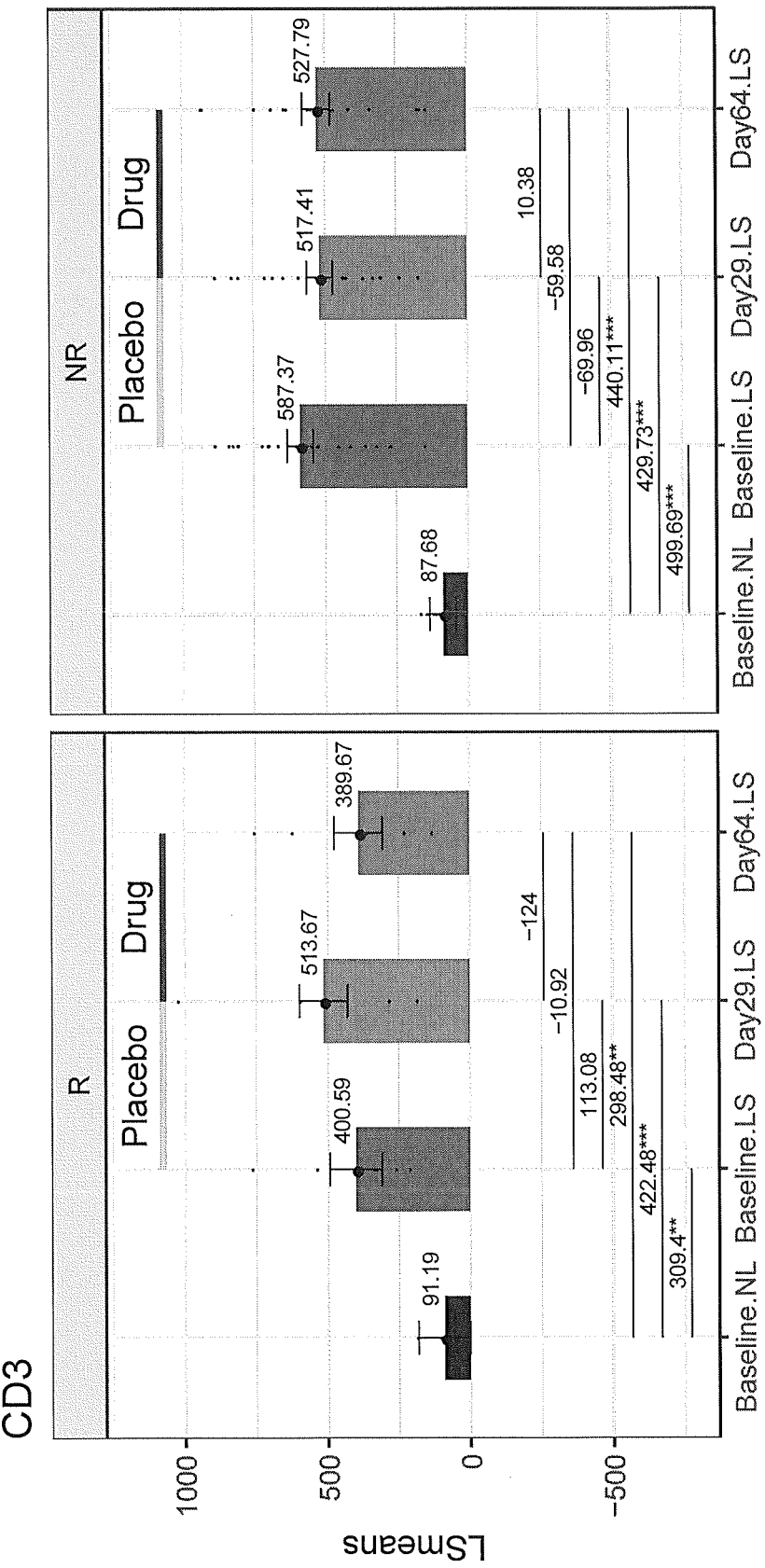
Figures 11A, 11B:
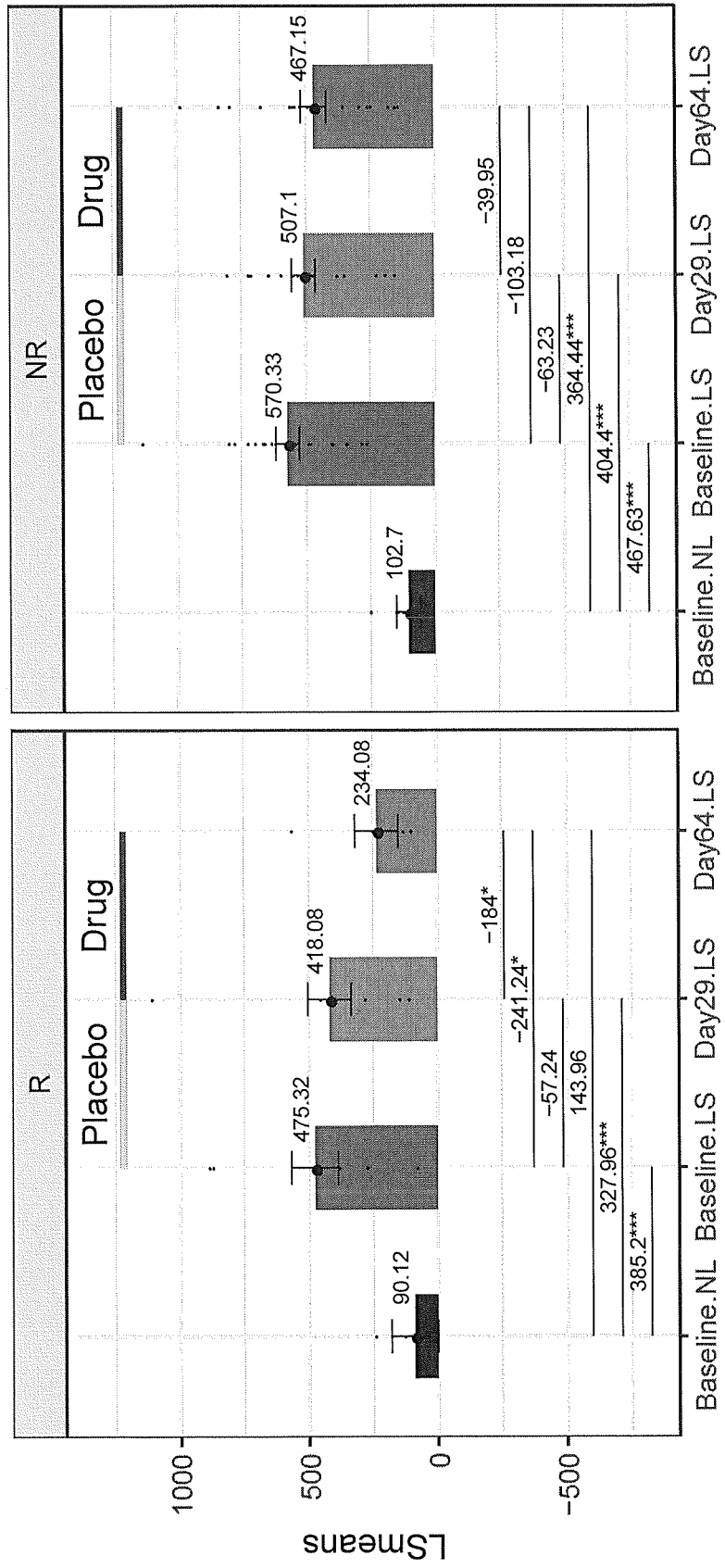
Figure 12:
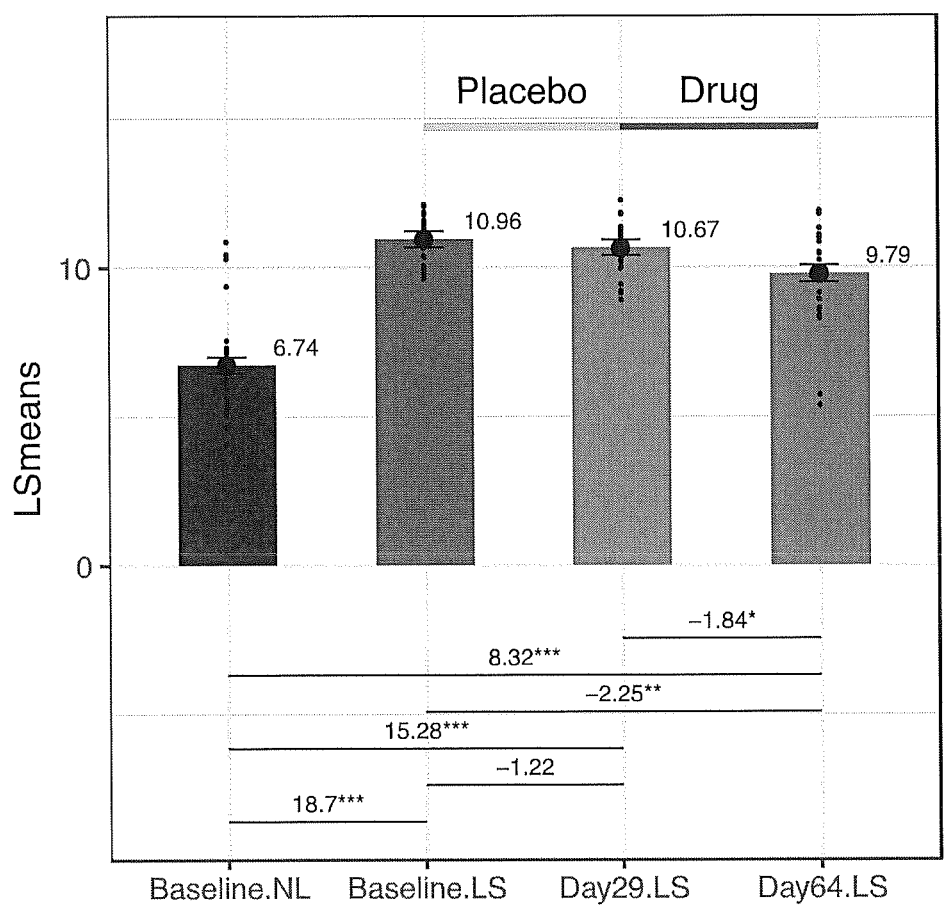
FIG. 12 shows graphs of expressed mRNA as assessed by RT-PCR demonstrating a statistically significant decline in expression of keratin-16 (KRT16) in lesional skin from the last day of placebo administration to the final day of PH-10 administration in the entire study population as least squared means (LSmeans) versus Baseline NL, Baseline LS, Day29LS, and Day64LS.

The present invention contemplates a method for the treatment of a hyperproliferative skin disorder; i.e., an increased rate of skin cell turnover in the epidermis discussed and exemplified hereinafter, that comprises administration of a therapeutically effective amount of a topical halogenated xanthene pharmaceutical composition, in combination with a therapeutically effective amount of a systemic anti-inflammatory agent.

The present invention also particularly contemplates a method for the treatment of psoriasis and eczema, that comprises administration of a therapeutically effective amount of a halogenated xanthene pharmaceutical composition, in combination with a therapeutically effective amount of a systemic immune system down-regulating agent.

The non-clinical topical application studies of $^{14}$C-labelled rose bengal discussed hereinafter show that the rose bengal remains mostly in the stratum corneum, with decreasing amounts present in epidermis and dermis. No radioactivity reached the plasma in the study conducted. Nonetheless, immune markers in the skin of clinical trial participants were down-regulated as measured by PCA of messenger RNA (mRNA).

These results are taken to mean that it is the keratinocytes that are affected by the topically-applied PH-10, whereas systemic drugs curb other gene expressions from deeper layers of the skin and from other distant organs. This indicates that one can treat different portions of the skin differently by using a topical treatment with a halogenated xanthene to treat keratinocytes and a systemic drug to treat other tissues.

Genes made less active (down-regulated) by PH-10 topical treatment include KRT16, CTLA4, IL19, S100A12, S100A7A, and IL36A. As can be seen from the results in FIGS. 2A, 3A, 4A, 5A, 6A and 7A, the lessened activity of those genes was statistically significant at least between baseline lesional skin and that lesional skin on Day 64 (i.e., after 4 weeks of PH-10 treatment).

In addition, PH-10 application for 4 weeks significantly (FC>1.5, p<0.05) down-regulated IL-17A, IL-22, IL-26, IL-36 and keratin mRNAs as assessed by RT-PCR, whereas a PCA analysis of gene array results showed a shift towards non-lesional skin with some post-treatment biopsies clustering within the non-lesional skin profile. Pathways significantly improved in lesional skin after PH-10 application included published psoriasis transcriptomes and cellular responses mediated by IL-17, IL-22 and interferons.

In a subset of subjects, referred to herein as "responders", "psoriasis related" genes including IL-23, IL-17, IL-22, S100A7, 11-19, IL-36 and CXCL1 were effectively normalized. That is, treated lesional skin had gene expression values for the above-mentioned genes in the same range as those present in baseline non-lesional skin. The immunohistochemistry in these responders indicated decreased expression of myeloid (CD11c+) dendritic cells and T-cells in treatment area biopsies.

The "responders" constituted 27 percent of the evaluable subjects. It is believed that the differences between "responders" and "non-responders" was a function of the regeneration stage of their keratinocytes at the time of PH-10 application. Kertatinocytes take an average of about three months (about 12 weeks) between their basal cell and shedding corneoycyte stages of differentiation.

Figure 21:
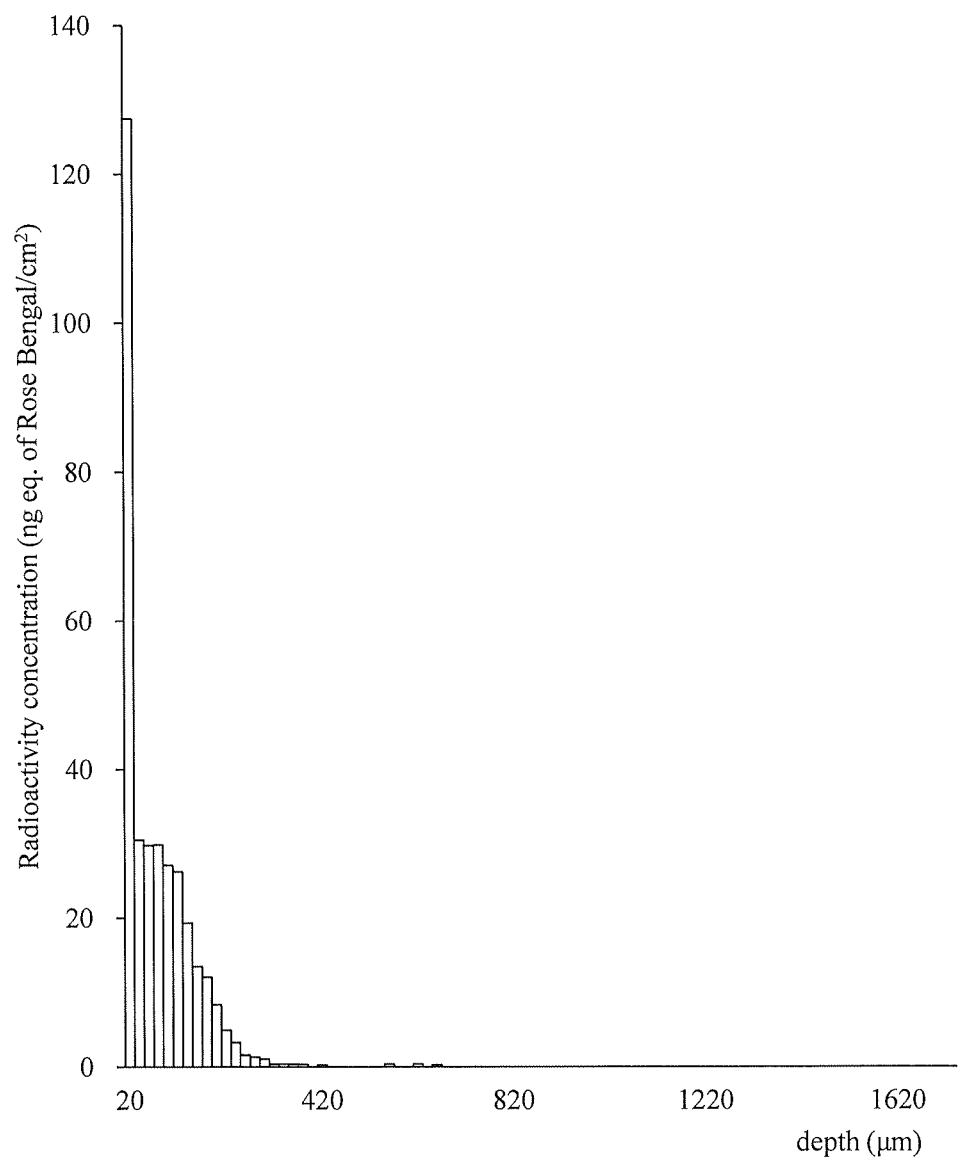
FIG. 21 is a graph showing radioactivity concentrations in the skin at 24 hours after a single topical application of $^{14}$C-Rose Bengal as a DMSO formulation applied to a 250 cm2 area on the dorsal skin of Goettingen Minipigs, a common model for human skin absorption studies.

The data provided herein and in FIG. 21 demonstrate that radiolabeled rose bengal when applied topically to the surface of Göttingen minipig skin did not penetrate the skin into the lower layers of tissue or into the plasma. Göttingen minipigs are a frequently used in pharmaceutical studies as a model for human skin. Nunoya et al., *J Toxicol Pathol* 2007 20:125-132. This localization of delivery of rose bengal to the stratum corneum and epidermis is shown in human skin in FIG. 13A.

The combination of targeting underlying disease using a systemic anti-inflammatory agent other than an NSAID, such as an immune system down-regulating agent treatment coupled with a locally-acting topical halogenated xanthene administration, is particularly attractive because it maximizes potential curative action on the skin, while diminishing inflammation and hyperproliferation. The inflammation and hyperproliferation responsible for the visible symptoms of the disease can therefore be reduced by the action of both medicaments operating on different inflammatory agents.

These aspects of treatment are especially important due to variable skin turnover rates and timing of up to 12 weeks needed to renew basement membranes and replenish skin. When combined with a systemic therapy that further addresses inflammation markers specific to the dermatologic disease, the effects on the underlying pathogenesis is synergistic, both at the site of topical administration and at untreated sites, including those proximal and distant to the application sites.

Many advantages accrue upon combining local topical therapy with a systemic targeted therapy, such as topical xanthene administration combined with a targeted biologic. The phrases "targeted systemic" and "systemic targeted" are used synonymously herein. Because topical xanthene administration has a uniquely disruptive effect on the inflammatory dermatoses, the combination of this modality with an approach that targets inflammatory pathways via an orthogonal path, such as those that target TNF-alpha, IL-17, IL-12 or IL-23 pathways or overexpression of genes involved in inflammation and hyperproliferation, can yield enhanced efficacy in the treated skin or gut.

For example, by using a systemic therapy to decrease inflammation in the wake of topical xanthene administration, the misfiring keratinocytes addressed with the topical treatment can be visible to the immune system in the wake of reduction of inflammation; response of any tissue not directly treated by PH-10 or similar halogenated xanthene composition can also be increased to immunologic activation resulting from the PH-10 treatment because the systemic therapy counters masking inflammation characteristic of the disease without interfering with development of the immune response from halogenated xanthene administration.

The reduction in hyperproliferation resulting from halogenated xanthene composition administration further augments these advantages by reducing immune suppression and physiologic demands from the inflamed tissue. Because the systemic targeted therapy is not required to achieve complete control or eradication of psoriatic or eczematous skin in this context, but rather serves to augment the activity of the local therapy, the systemic therapy can be administered at a reduced dose, thereby minimizing potential adverse effects and making the combined therapy safer and more attractive compared with prior systemic combinations. Addition of the keratinocyte-directed response resulting from the local therapy component provides a means to counter resistance problems that have plagued many systemic therapies, combating the repeated need to switch therapies when a systemic agent stops working.

In some cases it can be desirable to commence systemic targeted therapy prior to topical therapy, for instance when disease burden is very high or widespread, or when the disease is rapidly proliferating, potentially making effective administration of the local topical therapy difficult or less effective. In this manner, the systemic therapy can be used to control inflammation prior to administration of local therapy in order to enhance responsiveness of the disease to the local therapy. Treatment of residual disease with local therapy, such as topically-applied halogenated xanthenes, while it remains under control of the systemic therapy provides a means for elimination of residual lesional burden while stimulating long term immunity to recurrence in some instances, thereby improving ultimate outcome.

Examples of contemplated systemic combination therapies include small molecule (molecular weight about 900 or less) and proteinaceous active agents. Illustrative systemic active agents useful in a contemplated method of treatment include but are not limited to the following: local xanthene topical therapy combined with 1) one or more systemic inhibitors of TNF-alpha, such as adalimumab, certolizumab pegol, etanercept, golimumab, guselkumab or infliximab; 2)

one or more systemic IL-17A inhibitors, such as ixekizumab, brodalumab or secukinumab or a mixed IL-12/IL-23 inhibitor such as ustekinumab or risankizumab; 3) one or more IL-6 inhibitors such as sarilumab; 4) one or more of apremilast, crisaborole and other phosphodiesterase-4 (PDE4) inhibitors, and particularly PDE4C inhibitors that can be combined with local xanthene treatment such as with halogenated xanthene application on the skin or directly to the gut; 5) one or more systemic immune downregulating agents, including: methotrexate, cyclosporine, and azathioprine, can be beneficial via unmasking the driver of hyper-proliferation for local therapy.

Use of an NSAID that is a COX-1 and/or Cox-2 inhibitor such as aspirin, ibuprofen, naproxen, indomethacin, meloxicam, acetaminophen, celecoxib and the like as the systemic anti-inflammatory in conjunction with the halogenated xanthene is not contemplated.

Typically, monotherapy dose schedules are set by determining the maximum tolerated dose (MTD) in early-stage clinical trials. The MTD (or a close variation thereon) is then promulgated to later-stage clinical trials for assessment efficacy and more detailed assessment of safety. These MTDs frequently become the established therapeutic dose upon completion of clinical testing.

Exemplary therapeutically effective dosing amount schedules for a number of systemic agents that can be combined in the present invention with local topical therapy are provided in Table 1.

TABLE 1

Exemplary systemic immunomodulatory or targeted anticancer agents

| Systemic Agent | Typical Dose Schedule |
| --- | --- |
| adalimumab | 80 mg initial dose followed in 1 week by 40 mg every other week SQ |
| brodalumab | 210 mg subcutaneously (SC) at weeks 0, 1, and 2, then 210 mg SC q2wk |
| certolizumab pegol | 400 mg initially and at weeks 2 and 4 followed by 200 mg every other week or 400 mg Q4 weeks maintenance SQ |
| etanercept | 50 mg twice weekly for 3 months followed by 50 mg once weekly SQ |
| golimumab | 50 mg once a month SQ |
| guselkumab | 100 mg subcutaneous injection once every 8 weeks, after starter doses at weeks 0 and 4 |
| infliximab | 5 mg/kg given as an IV induction regimen at 0, 2, and 6 weeks followed by a maintenance regimen of 5 mg/kg every 8 weeks thereafter |
| ixekizumab | 160 mg initial dose followed Q2 weeks with 80 mg until week 12 then 80 mg Q4 weeks SQ |
| sarilumab | 200 mg every 2 weeks as a subcutaneous injection |
| secukinumab | 300 mg every week for 4 weeks then 300 mg every 4 weeks SQ |
| ustekinumab | Less than 100 kg: 45 mg initially, week 4 followed by 45 mg every 12 weeks SQ More than 100 kg: 90 mg initially, week 4 followed by 90 mg every 12 weeks SQ |
| apremilast | Titrated dose over 5 days to work up to 30 mg twice daily PO |
| methotrexate | Weekly single oral, IM or IV 10 to 25 mg per week or divided 2.5 mg dose at 12 hour intervals for three doses |
| cyclosporine | Initial dose 2.5 mg/kg/day taken twice daily as divided (BID); dose titrated up to 4 mg/kg/day BID if response and laboratory abnormalities don't ensue. |
| azathioprine | Used off label for skin diseases, 1.0 mg/kg oral or IV as a single dose or twice a day, dose maximum is 2.5 mg/kg/day. |

Because of additive effects, the combination therapies and method of treatment of the present invention generally permit use of the targeted systemic agent at a level at or below the typical dose schedule for that systemic agent, such as those described in Table 1, when used with a local topical therapy, such as that described below. However, the therapeutically effective dosing amount schedules provided in Table 1 provide a useful guide for beginning treatment from which therapeutically effective dosage amounts can be titrated to lessened amounts as seen appropriate by the physician caring for a given patient.

The targeted systemic anti-inflammatory therapy is administered orally or parenterally, typically utilizing a commercially available composition such as those exemplified in Table 1. Therapeutically effective dosing amounts of systemic targeted pharmaceutical products not listed in Table 1 can be obtained from the labels of such products.

The two medicaments can be administered substantially simultaneously, separated by one or more hours, days or weeks. In addition, the systemic therapy can be initiated weeks or months as a stabilizing regimen before the local keratinocyte-acting halogenated xanthene administration.

Delivery of the halogenated xanthene component of a contemplated composition is most favorable when the composition has a pH value close to physiologic pH (i.e., approximately pH 7), and especially when the pH is greater than about 4, thereby assuring that a halogenated xanthene remains in dibasic form in the composition. Thus, in a preferred embodiment, the pH value of the composition is about 4 to about 10, and more preferably about 5 to about 9, and most preferably about pH 6 to about pH 8.

A halogenated xanthene is preferably dissolved or dispersed in a hydrophilic vehicle to maximize preference for partitioning of the halogenated xanthene component into skin tissue. Accordingly, in a preferred embodiment, the vehicle contains a minimum of non-hydrophilic components that might interfere with such partitioning.

A preferred formulation of the topically-applicable composition contains, in a hydrophilic, preferably water-containing, vehicle:

1) a halogenated xanthene such as of rose bengal (4,5,6,7-tetrachloro-2',4',5',7'-tetraiodofluorescein) that is particularly preferred, or another halogenated xanthene, including erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein in an appropriate pharmaceutical composition.

A preferred form, rose bengal disodium, has the following formula:

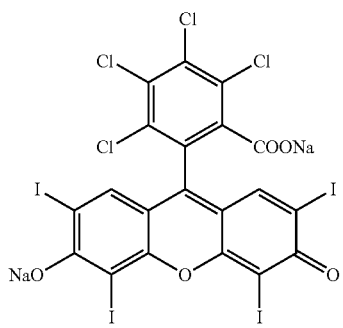

Certain details of this preferred embodiment for the local topical composition are described in U.S. Pat. Nos. 5,998,597, 6,331,286, 6,493,570, and 8,974,363, whose disclosures are incorporated by reference herein in their entireties. This preferred embodiment of the present invention is described here with particular relevance to psoriasis and eczema.

However, the present invention can also find application for the treatment of other hyperproliferative skin or epithelial diseases including, but not limited to, ulcerative colitis, Crohn's disease, acktinic keratosis, acne vulgarius, and no limitation is intended thereby. Exemplary indications further include treatment for: atopic dermatitis (eczema) and psoriasis that are chronic, remitting-relapsing inflammatory dermatoses; psoriasis and pustular psoriasis; Reiter's Syndrome; skin ulcers, including stasis dermatitis, stasis ulcers, ischemic ulcers, sickle cell leg ulcers, diabetic ulcers, inflammatory ulcers; eczematous disease and eczematous reaction; various ichthyoses; atopic dermatitis; benign and malignant proliferative disorders, such as benign epithelial tumors and hamartomas; premalignant and malignant epithelial tumors, including actinic keratoses, basal cell carcinoma, squamous cell carcinoma, and keratoacanthoma; benign and malignant adnexal tumors; tumors of pigment-producing cells, including malignant melanoma, solar lentigines, Nevi, and cafe-au-lait; sarcomas; lymphomas; vascular disorders; such as hemangiomas and port wine stain; microbial infection, such as bacterial, fungal, yeast, parasitic or other infections; warts; and acne.

A contemplated halogenated xanthene-containing composition typically contains a therapeutically effective amount of a halogenated xanthene. An exemplary therapeutically effective amount of a halogenated xanthene is a concentration of approximately 0.0001% to about 0.01% by weight, and even more preferably at about 0.0005% to about 0.005%, and most preferably that this concentration is approximately 0.001% to approximately 0.05% of a halogenated xanthene. Application of a dose of an above-described contemplated halogenated xanthene-containing composition as discussed hereinafter provides a therapeutically effective dose of the composition.

2) One or more viscosity builders, collectively a viscosity builder or just "builder", at a level sufficient to achieve a composition viscosity of about 10 to about 1000 cps at ambient room temperature such as 25° C. The viscosity builder is typically selected from the group including cellulose and cellulose derivatives, such as starch, alginates, and various carboxymethylcelluloses and derivatives thereof, especially those of medium to high viscosity, such as USP carboxymethylcellulose.

Other contemplated builders include the neutralized or partially neutralized poly(acrylic acid or methacrylic acid) homopolymers and co-polymers such as those sold under the name Carbapol® 934P that is described in U.S. Pat. Nos. 2,798,053, 2,909,462 and 3,330,729, and the higher molecular weight polymer that is sold under the name Carbapol® 940. Carbapol® 934P is said to be prepared from acrylic acid that is cross-linked with about 0.75 to about 2 percent by weight of a polyallyl polyether such as polyallyl sucrose or polyallyl pentaerythritol that are said to contain an average of at least three allyl groups per molecule, wherein the allyl groups are bonded by ether linkages.

The builder is present in an amount to provide a viscosity of the composition of about 10 to about 1000 centipoise (cps) at a temperature of 25° C. and one atmosphere. More preferably, the viscosity builder provides a viscosity of about 50 to about 500 cps, and even more preferably that viscosity is about 75 to about 250 cps.

3) A third ingredient is a water-soluble electrolyte selected from sodium, potassium, calcium and magnesium chlorides, phosphates, and nitrates, wherein the electrolyte is present at a concentration of about 0.1 to about 2% by weight, or alternately at a level sufficient to provide an osmolality of about 100 mOsm/kg to about 600 mOsm/kg. More preferably, the osmolality of the halogenated xanthene composition is greater than 250 mOsm/kg, and most preferably approximately 300-500 mOsm/kg.

The electrolyte is preferably sodium chloride. The electrolyte is preferably present at a concentration of about 0.5 to about 1.5% by weight, and even more preferably at a concentration of about 0.8 to about 1.2%, and most preferably at a concentration of approximately 0.9% as is present in physiological saline.

The hydrophilic, preferably water-containing, vehicle is preferably only water that meets the criteria for use in a topical composition. Up to about 20 percent by volume of the vehicle can be one or more $C_1$-$C_6$ mono- or polyhydric alcohols such as methanol, ethanol, propanol, isopropanol, butanol, sec-butanol, glycerol, ethylene glycol, propylene glycol, 1,2-butanediol, 2,3-butanediol, erythritol, threitol, trimethylolpropane, sorbitol and the like. More preferably, an alcohol is present in a contemplated composition at less than about 10 percent by volume of the vehicle, and more preferably at less than about 5 percent by volume.

A typical therapeutically effective dosage of a halogenated xanthene pharmaceutical composition as discussed above is administered topically at about 0.5 mL/100 cm$^2$ lesional skin to about 2 mL/100 cm$^2$ lesional skin, and most preferably about 1 mL/100 cm$^2$ lesional skin. Such doses typically correspond to a patient cumulative dose of about 1 mg to about 15 mg of halogenated xanthene (which are significantly lower than those doses used for diagnostic liver tests or oncology applications).

The amount of skin surface that can be treated has no known limit. However, due to difficulty in application, the scalp is often excluded. Other exclusions are safety exclusions for the biopsies, and there is no reason known that would preclude applying a halogenated xanthene pharmaceutical composition to the face.

One of the largest treatment areas to which a halogenated xanthene pharmaceutical composition has been applied was 600 cm$^2$. The total skin surface in an adult is about 20,900 cm$^2$. Any affliction of more than 30% of the skin surface is considered severe (6,270 cm²), and that is a likely maximum that any topical treatment could cover. There is also the issue of un-erupted skin (not visible yet) that is hyper-proliferating.

Looked at alternatively, the present invention utilizes a compound of Formula 1, below, in which $R_1$ is independently F, Cl, Br, I, H or $C_1$-$C_4$ alkyl; $R_2$, $R_3$, $R_4$, and $R_5$ are independently Cl, H or I with at least one substituent selected from $R_2$, $R_3$, $R_4$, $R_5$ being I and at least one is Cl or H; and $R_6$ is independently H or $C_1$-$C_4$ alkyl; $R^{11}$ is H or $C_1$-$C_4$ alkyl; $R^{12}$ is H or $C_1$-$C_7$ acyl; and all (a) tautomeric forms; (b) atropisomers, (c) closed lactone forms as depicted in Formula 2 (below), (d) enantiomers of lactone forms depicted in Formula 2, and (e) pharmaceutically acceptable salts thereof.

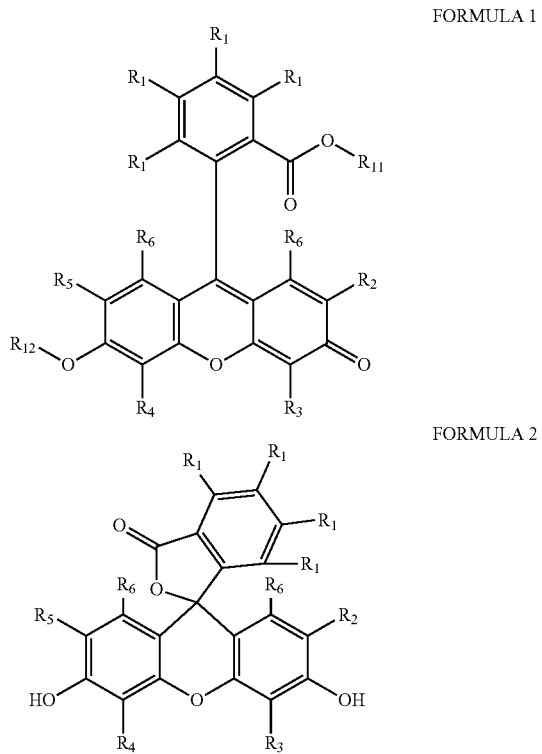

FORMULA 1

FORMULA 2

The terms "physiologically acceptable salt" and "pharmaceutically acceptable salt" in their various grammatical forms refer to any non-toxic cation such as an alkali metal, alkaline earth metal, and ammonium salt commonly used in the pharmaceutical industry, including the sodium, potassium, lithium, calcium, magnesium, barium, ammonium and protamine zinc salts, which can be prepared by methods known in the art. A contemplated cation provides a water-soluble xanthene salt. Preferably, the salts are sodium, potassium, calcium and ammonium in either the mono or dibasic salt form. The reader is directed to Berge, *J. Pharm. Sci.* 1977 68(1):1-19 for lists of commonly used physiologically (or pharmaceutically) acceptable acids and bases that form physiologically acceptable salts with pharmaceutical compounds.

The pH value of the halogenated xanthene pharmaceutical composition can be regulated or adjusted by any suitable means known to those of skill in the art. The composition can be buffered or the pH value adjusted by addition of acid or base.

As a halogenated xanthene, or physiologically acceptable salt thereof, are weak acids, depending upon halogenated xanthene concentration and/or electrolyte concentration, the pH value of the composition may not require the use of a buffer and/or pH value-modifying agent. It is especially preferred, however, that a composition be free of buffer, allowing it to conform to the biological environment once administered.

It is also preferred that the pharmaceutical composition not include any preservatives, many of which can deleteriously interfere with the pharmaceutical composition or formulation thereof, or may complex or otherwise interact with or interfere with the delivery of the halogenated xanthene composition active component. To the extent that a preservative is used, imidurea is a preferred preservative as it does not interact with halogenated xanthenes, either in the pharmaceutical composition or upon administration.

When utilized as a single active ingredient treatment, use of a halogenated xanthene pharmaceutical composition has been recommended to be followed by active irradiation of the skin area to which the composition has been applied using a visible light source. This is taught in U.S. Pat. No. 8,974,363. Post halogenated xanthene pharmaceutical composition application active irradiation with visible light is not needed in the present treatment method, and is preferably not used.

The medicament pair disclosed herein are broadly applicable to improved treatment of various conditions affecting the skin and related organs of humans and other animals. The halogenated xanthene portion of the medicament pair can be applied directly to, or substantially proximal to, tissues to be treated, including those of the skin, nails, scalp and oral cavity, whereas the systemic portion is administered systemically as orally, buccally, intravenously, intramuscularly, subdermally and the like well-known methods of parenteral administration.

According to a preferred embodiment of the present invention, there is provided a method for the treatment of hyper-proliferative skin disorders in a patient, such as psoriasis or eczema. That method comprises treatment of a patient (a subject in need) with a local topical therapy combined with one or more systemic therapies, wherein said local topical therapy comprises surface administration of a therapeutically effective amount of a pharmaceutical composition comprising a vehicle containing halogenated xanthene such as 4,5,6,7-tetrachloro-2',4',5',7'-tetraiodofluorescein (i.e., rose bengal), or a physiologically acceptable salt thereof dissolved or dispersed therein.

The preferred concentration of halogenated xanthene and/or dose of its pharmaceutical composition is dependent upon factors including, but not limited to, amount of diseased skin, number and location of lesional skin or plaques. For gut disorders, such as ulcerative colitis or Crohn's disease, the xanthene preparation can be formulated for oral administration and ingested.

The halogenated xanthene composition is usually administered topically although it can be formulated for oral administration and so administered as noted above for treatment of gut disorders, such as ulcerative colitis or Crohn's disease.

A contemplated treatment method is utilized on a mammal in need thereof. A treated mammal can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Each contemplated composition is typically administered repeatedly in vivo to a mammal in need thereof until the treated skin condition is diminished to a desired extent, such as cannot be detected. Thus, the administration to a mammal in need can occur a plurality of times within one day, daily, weekly, monthly or over a period of several months to several years as directed by the treating physician.

Figure 17:
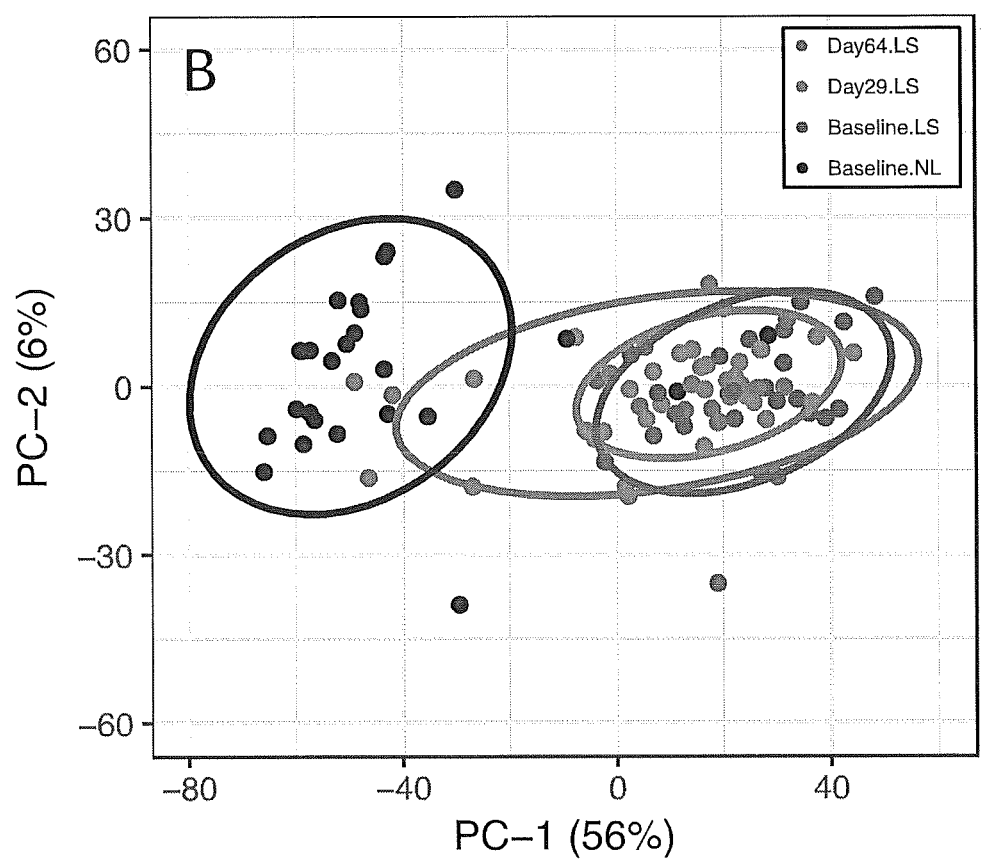
FIG. 17 shows PCA of gene array results for non-lesional (NL) skin and lesional (LS) psoriasis skin at baseline (BL), day 29 and day 64, DEG FCH>2 and fdr<0.05, for all evaluable patients, analyzed similarly to the data presented in Kim et al., *J Invest Dermatol* 2016 136:2173-2182 and Krueger et al., *J Allergy Clin Immunol* 2015 136(1):116-124.

Results:

Vehicle treatment for 4 weeks did not significantly alter expression of core IL-23/IL-17-modulated genes or the overall disease transcriptome (using a principle component analysis, PCA). However, 4 weeks of treatment with PH-10 significantly (FC>1.5, p<0.05) (FC=Fold Change; p=statistical p-value) down-regulated IL-17A, IL-22, IL-26, IL-36, and keratin 16 mRNAs as assessed by RT-PCR. A PCA analysis of gene array results showed a shift towards non-lesional skin with some post-treatment biopsies clustering within the non-lesional skin profile (FIGS. 17 and 18).

Figure 18A:
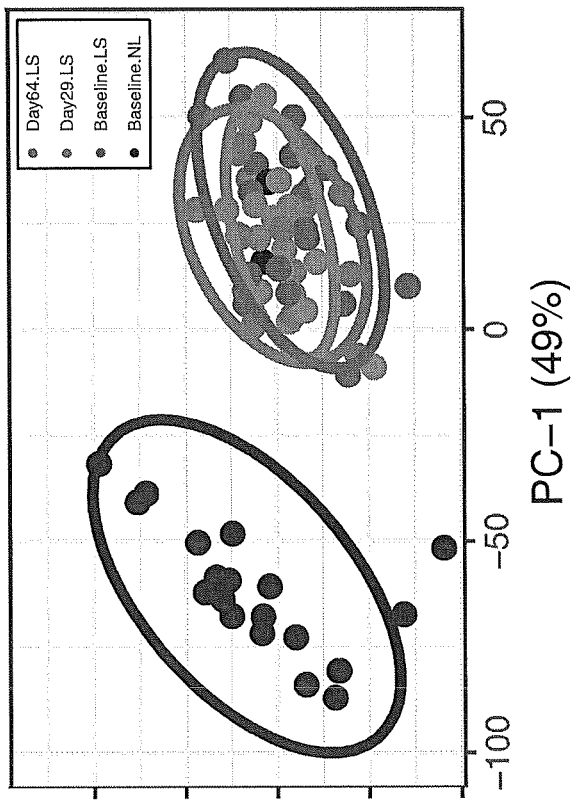
FIGS. 18A and 18B show PCA microarray data for all genes in the dataset. Those data were used to identify a cohort of "Molecular Responders", patients with PC-1 values for D64/LS lower than the 90th percentile for PC-1 values for baseline for non-lesional (BL/NL) skin. For these Responders, gene expression in LS tissue after PH-10 treatment is similar to NL skin at baseline. Data are shown for DEG FCH>2 and fdr<0.05.
Figure 18B:
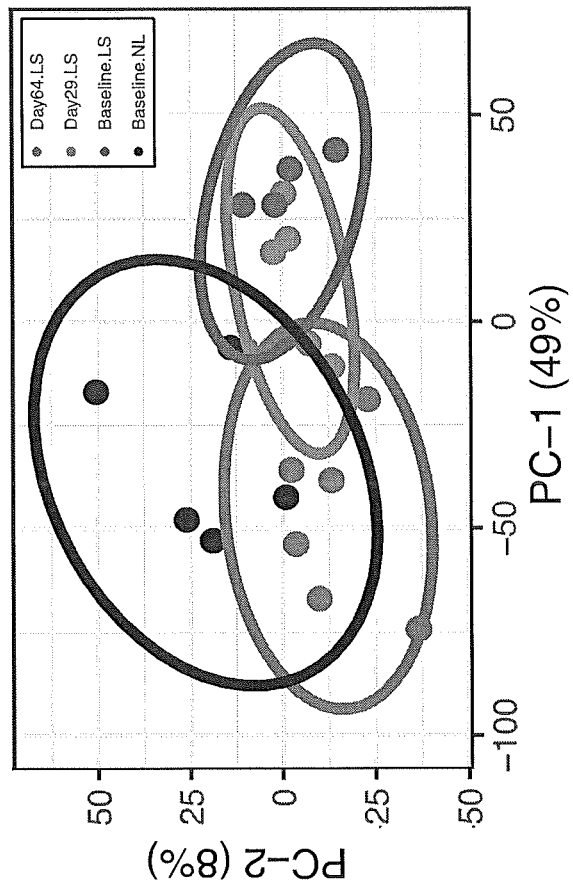

Pathways that were significantly improved by PH-10 administration included published psoriasis transcriptomes and cellular responses mediated by IL-17, IL-22, and interferons. To strengthen analysis of immune and psoriasis-related gene modulation by PH-10, patients were divided into responders vs. non-responders based on the PCA analysis after 4 weeks of treatment (comparing to non-lesional skin at baseline) (FIGS. 18A and 18B).

Using this approach, more than 500 disease-related genes were down-regulated after 4 weeks of treatment with PH-10 and expression of a wide-range of central "psoriasis related" genes including IL-23, IL-17, IL-22, S100A7, IL-19, IL-36, and CXCL1 were effectively normalized; i.e., treated lesional skin had values in the same range as baseline non-lesional skin (FIGS. 19A and 19B).

Figure 20A:
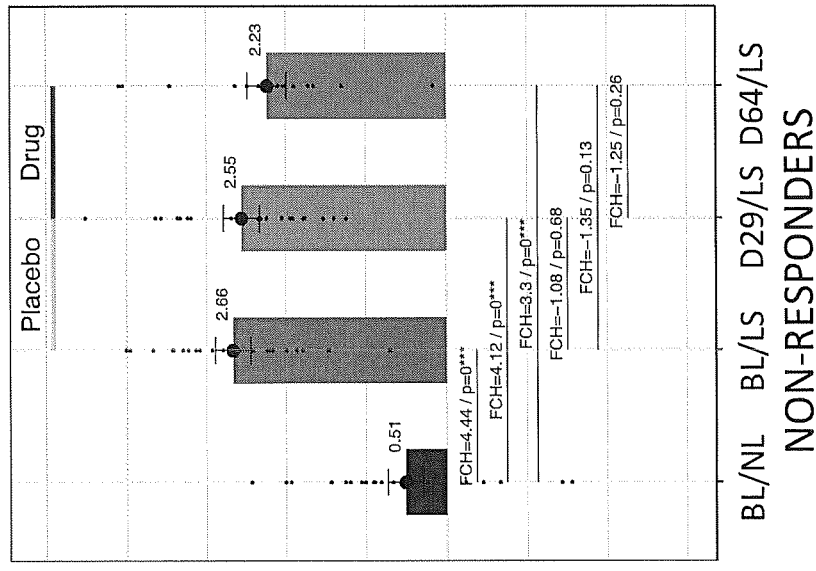
FIGS. 20A and 20B are graphs showing ICOS expression by molecular response cohort in non-lesional (NL) skin and lesional (LS) psoriasis skin at baseline (BL), day 29 (D29) and day 64 (D64) in Responders (20A) and Non-Responders (20B)
Figure 20B:
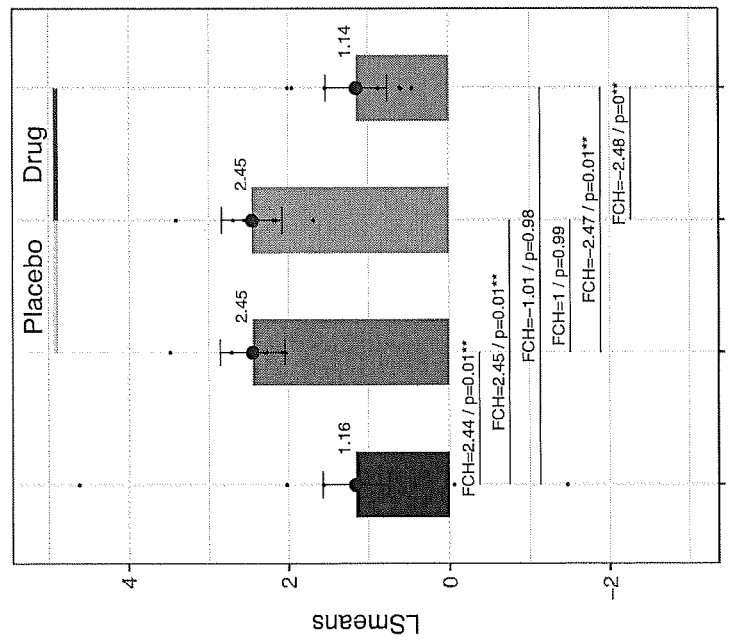

Decreased expression of T-cell activation markers including ICOS and CTLA4 were also measured, showing changes that were paralleled by decreases in myeloid (CD11c$^+$) dendritic cells and T-cells using IHC measures (FIGS. 20A and 20B). Those two markers were significantly reduced by day 64 vs. day 29.

Conclusions

These results establish that PH-10 has highly significant ability to modulate psoriatic inflammation, including key cytokine drivers of the disease, but only a subset of patients revert the lesional phenotype to that of non-lesional skin. This type of "mixed" response outcome occurs with other topical or systemic drugs now approved for psoriasis, highlighting a need to personalize treatments and potentially to have predictive response biomarkers for individual drugs. Importantly, the vehicle did not elicit any detectable changes in these same markers in lesional biopsies.

Materials and Methods

Introduction

Figure 13A:
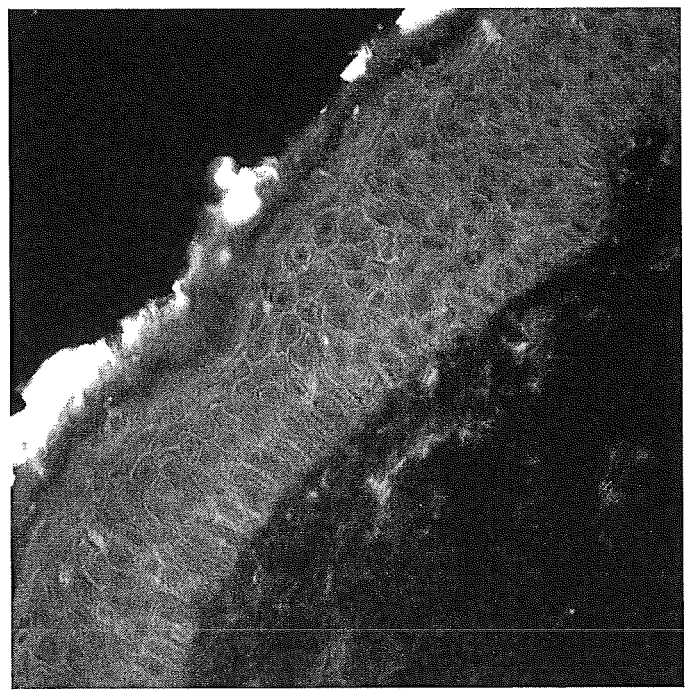
FIG. 13A and FIG. 13B are confocal fluorescence micrographs of normal human skin: topical PH-10 (left) vs H&E staining (right). From Wachter et al., *Lasers Surg Med* 2003 32:101.
Figure 13B:
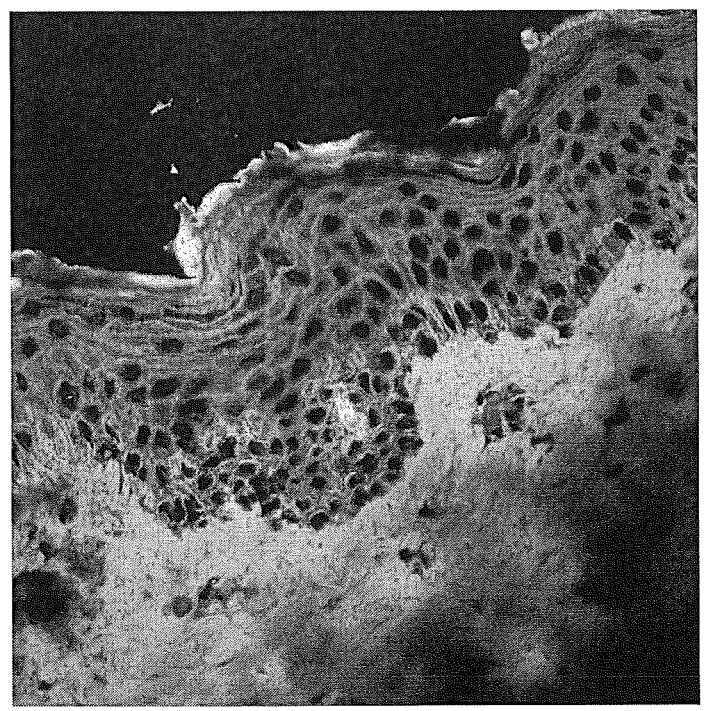

PH-10 is a topical hydrogel formulation that yields selective delivery of Rose Bengal Disodium (RB) to epithelial tissues (FIGS. 13A and 13B). RB is a fluorescein derivative capable of producing singlet oxygen upon photo-activation, but its therapeutic mechanism in psoriasis vulgaris has not been previously established.

Study Population

Thirty patients were enrolled in a phase 2 clinical trial conducted at 3 centers in the United States; eligible patients presented with mild to moderate psoriasis lesions on the trunk or extremities amenable to biopsy, at least 5 cm in diameter. Enrolled subjects were predominately male (63%) and white (77%) with median age of 45 and age ranging from 18-70. The majority of subjects had psoriasis for longer than 5 years (93%) presenting at baseline with moderate disease (73%) according to the investigator plaque assessment scoring. Twenty-one subjects completed the entire study course of 28 days of vehicle administration, 7 day biopsy recovery interval, followed by 28 days of PH-10 application and had full sets (baseline: lesional and non-lesional; Day 29 and Day 64 lesional only) of evaluable biopsies. An additional subject had stark differences in lesional biopsies between day 29 and day 64, and was included in the included in the responder analysis group.

Immunohistochemistry

Immunohistochemistry was performed for leukocytes for all subject biopsies. Frozen tissue sections were stained with haematoxylin (Thermo fisher Scientific) and eosin (Shandon) or with murine anti-human monoclonal antibodies (Fuentes-Duculan et al., *J Invest Dermatol* 2010 130:2412-2422). Biotin-labeled horse anti-mouse antibodies (Vector Laboratories) were used to amplify the primary signal with an avidin-biotin complex and developed with chromogen-3-amino-9-ethylcarbazole (Sigma-Aldrich). Positively stained cells per millimeter were manually counted using image analysis software (Image J, version 1.38 x, National Institutes of Health), and reported per mm linear length of the epidermis (Fuentes-Duculan et al., *J Invest Dermatol* 2010 130:2412-2422).

Microarray

RNA was extracted from full-thickness skin biopsies (NL, LS, baseline; LS days 29 and 64) of 21 subjects. Patients were classified as responders based on PCA analysis in comparison to non-lesional biopsies at baseline. RNA was extracted using the RNeasy® Mini Kit (Qiagen, Valencia, Calif.). For each HGU 133 2.0 Affymetrix® gene chip, 2 µg total RNA was reverse transcribed, amplified and labeled (Guttman-Yassky et al., *J Immunol* 2008; 181(10):7420-7427). Studies were conducted in compliance with Minimum Information About a Microarray Experiment guidelines.

The analysis was conducted using R software (R-project.org) with bioconductor packages (bioconductor.org). CEL files were scrutinized for spatial artifacts by using the Harshlight package (Suarez-Farinas et al., *BMC Bioinformatics* 2005 6:294). Classic microarray quality control report was obtained by using the affyQCReport package. Expression values were obtained by using GCRMA algorithm.

Probe-set with standard deviation (SD) greater than 0.1 and expression values greater than 3 in at least 2 samples were kept for further analysis (13405 probe-sets). Expression values were modeled using mixed effect models with Time as fixed effect and Patient as a random factor. Model estimation and hypothesis testing were conducted in the framework of limma. Comparisons of interest were assessed using moderated-t test, and resulting p-values were adjusted for multiples hypothesis using Benjamini-Hochberg approach. Probe-sets with fold change (FCH) larger than 2 and false discovery rate (FDR) smaller than 0.05 were selected as PH-10 modulated genes. PT-PCR was conducted for several genes, as previously described.

Skin Penetration Study $^{14}$C-Rose Bengal (1 mg/mL in DMSO) was applied to a 250 cm2 area on the dorsal skin of Goettingen Minipigs, a common model for human skin absorption studies. Radioactivity was collected in the plasma collected from the exposed animals at regular intervals starting at 0.5 hours post dose. Similarly, urine and feces were collected from the cages of the animals at appropriate time points.

At the conclusion of 168 hours, the application site of the skin was collected. All of these samples were evaluated for radioactivity and a calculation was made as to the cumulative fate of the radioactive element per dose. Histograms were prepared from the radioactivity measured at 20 um depth intervals in the skin.

The results of this study indicated that no radioactivity was collected in any tissue other than the skin. No radioactivity was recovered in the plasma at any time point indicating no systemic exposure after topical administration. After 24 hours, the radioactivity concentration in the skin was maximal in the stratum corneum and decreased depth-dependently into the epidermis with very little radioactivity seen in the epidermis and dermis.

Figure 14:
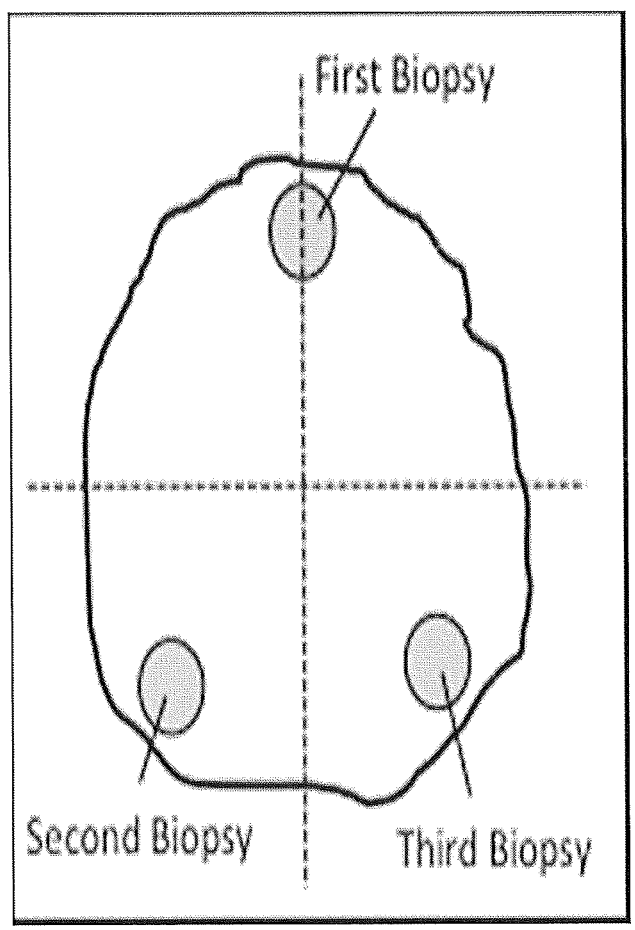
FIG. 14 is a schematic showing the outline of a plaque and sequential biopsy locations as marked for assessment of effect of 28 consecutive days of vehicle (second biopsy, on study day 29) and PH-10 (third biopsy, on day 64) vs baseline (first biopsy) in a single plaque; adjacent normal skin collected concurrently with first biopsy at day −7/baseline.
Figure 15:
FIG. 15 contains photos at two magnifications of a single target plaque at baseline (left), after vehicle (center) and after PH-10 (right) applications.

Methods:

A mechanistically-focused study of PH-10 in 30 patients with psoriasis vulgaris was made using sequential vehicle and active drug treatment for 4 weeks each (registered clinical trial NCT02322086). Skin biopsies were collected before treatment (baseline) and at the end of vehicle (day 29) and PH-10 treatment (day 64) (FIGS. 14 and 15).

Figure 16B:
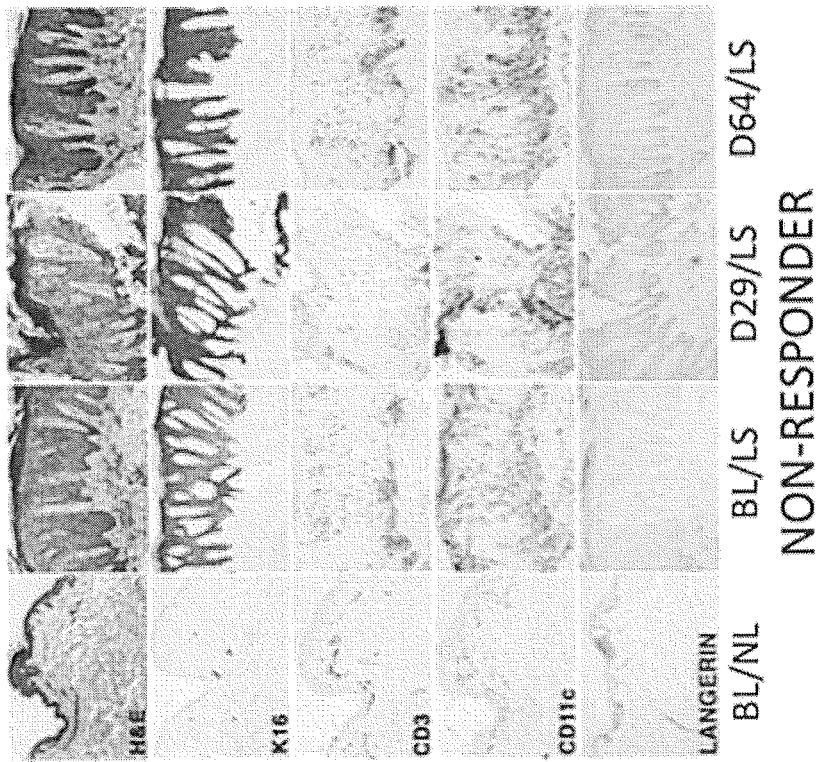
FIGS. 16A and 16B are photomicrographs of immunohistochemical (IHC) staining of non-lesional (NL) and lesional (LS) psoriasis skin at baseline (BL), after vehicle (D29) and after PH-10 (D64) for a responder (16A) and a non-responder in the study (16B)
Figure 16A:
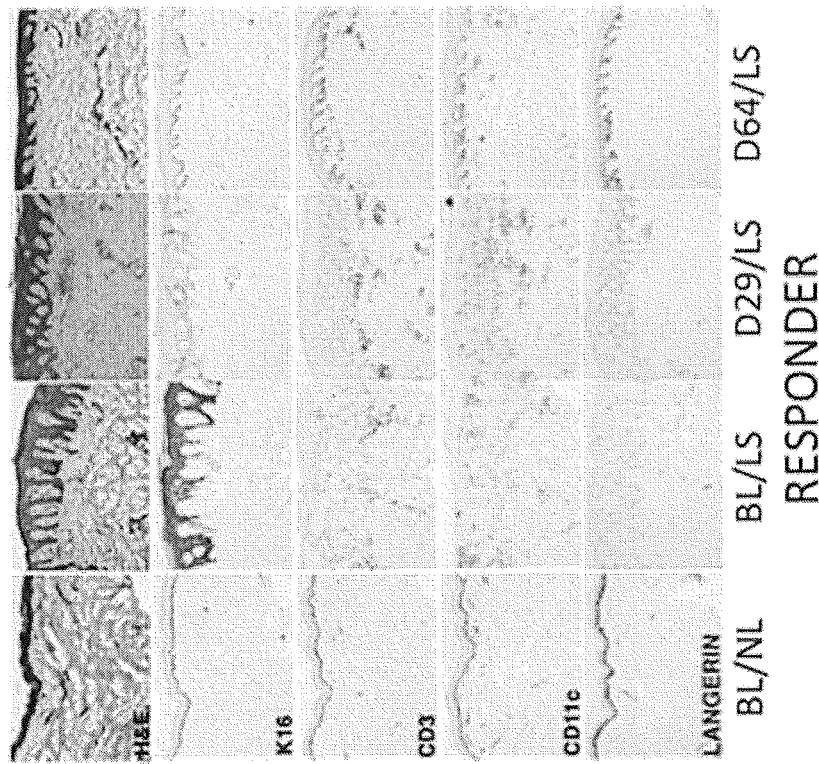

Effects of vehicle vs PH-10 treatment were assessed on cellular immune infiltrates, driver cytokines of psoriasis and the overall disease transcriptome using immunohistochemistry (FIG. 16) and gene-expression profiling with Affymetrix® U133 2.0Plus arrays and RT-PCR (FIG. 17 through FIGS. 20A and 20B).

Each of the patents, patent applications and articles cited herein is incorporated by reference. The articles "a" and "an" are used herein to refer to one or to more than one (i.e., to at least one) of the grammatical object of the article. Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art. For example, in addition to applicability to skin, as described here in detail, the present invention is applicable to disease of other epithelial tissue, such as that of the lining of the gut or reproductive tract.

The invention claimed is:

1. A method for the treatment of psoriatic tissue in a mammal that comprises topically administering to said mammal a therapeutically effective amount of rose bengal or a pharmaceutically acceptable salt thereof dissolved or dispersed in hydrophilic pharmaceutical composition, in combination with an orally administered therapeutically effective amount of apremilast.

2. The method according to claim 1, wherein said topical pharmaceutical composition contains the rose bengal or pharmaceutically acceptable salt thereof at a concentration of about 0.0001% to about 0.01% by weight.

3. The method according to claim 2, wherein said topical pharmaceutical composition contains a viscosity builder that is present in an amount to provide a viscosity of the composition of about 10 to about 1000 centipoise (cps) at a temperature of 25° C. and one atmosphere.

4. The method according to claim 3, wherein said topical pharmaceutical composition contains a water-soluble electrolyte present at a concentration of about 0.1 to about 2% by weight, or alternately, at a level sufficient to provide an osmolality of greater than approximately 100 mOsm/kg to about 600 mOsm.

5. The method according to claim 1, wherein said psoriatic tissue is skin.

6. The method according to claim 1, wherein said rose bengal or a pharmaceutically acceptable salt thereof is rose bengal disodium.

* * * * *